US009658227B2

(12) United States Patent
Mercier et al.

(10) Patent No.: US 9,658,227 B2
(45) Date of Patent: May 23, 2017

(54) RECOMBINANT GRA ANTIGENS AND THE USE OF SAME FOR EARLY DIAGNOSIS OF TOXOPLASMOSIS

(71) Applicants: UNIVERSITE JOSEPH FOURIER-GRENOBLE 1, St. Martin d'Hères (FR); CENTRE HOSPITALIER UNIVERSITAIRE GRENOBLE, La Tronche (FR)

(72) Inventors: Corinne Mercier, La Tronche (FR); Marie-France Delauw, Grenoble (FR); Hervé Pelloux, Bernin (FR); Hélène Fricker-Hidalgo, Vaulnaveys le Haut (FR)

(73) Assignees: Universite Joseph Fourier—Grenoble 1, St. Martin d'Hères (FR); Centre Hospitalier Universitaire Grenoble, La Tronche (FR)

( * ) Notice: Subject to any disclaimer, the term of this patent is extended or adjusted under 35 U.S.C. 154(b) by 0 days.

(21) Appl. No.: 14/435,373

(22) PCT Filed: Oct. 16, 2013

(86) PCT No.: PCT/EP2013/071578
§ 371 (c)(1),
(2) Date: Apr. 13, 2015

(87) PCT Pub. No.: WO2014/060448
PCT Pub. Date: Apr. 24, 2014

(65) Prior Publication Data
US 2015/0293090 A1 Oct. 15, 2015

(30) Foreign Application Priority Data

Oct. 16, 2012 (FR) ...................... 12 59850

(51) Int. Cl.
*G01N 33/569* (2006.01)
(52) U.S. Cl.
CPC ... *G01N 33/56905* (2013.01); *G01N 2333/45* (2013.01); *G01N 2469/20* (2013.01)
(58) Field of Classification Search
None
See application file for complete search history.

(56) References Cited

U.S. PATENT DOCUMENTS

| 5,824,788 A | 10/1998 | Cesbron et al. |
| 2003/0119053 A1 | 6/2003 | Maine et al. |

FOREIGN PATENT DOCUMENTS

| FR | 2702491 A1 | 9/1994 |
| FR | 2714074 A1 | 6/1995 |

OTHER PUBLICATIONS

Holec-Gsior et al., (Clinical Microbiology and Infection, (May 2009) vol. 15, Supp. S4, pp. S281 Abstract No. P1059; 19th European Congress of Clinical Microbiology and Infectious Diseases (ECCMID). Helsinki, Finland. May 16, 2009-May 19, 2009).*

Brown, Erik D., et al.; "A systematic review of neonatal toxoplasmosis exposure and sensorineural hearing loss," International Journal of Pediatric Otorhinolaryngology, 73(5), Feb. 11, 2009, pp. 707-711.

Elyasi, Hossein, et al.; "Use of Dense Granule Antigen GRA6 in an Immunoglobulin G Avidity Test to Exclude Acute *Toxoplasma gondii* Infection during Pregnancy," Clinical and Vaccine Immunology, vol. 17, No. 9, Sep. 2010, pp. 1349-1355.

Ferrandiz, Josette, et al.; "Limited Value of Assays Using Detection of Immunoglobulin G Antibodies to the Two Recombinant Dense Granule Antigens, GRA1 and GRA6 Nt of *Toxoplasma gondii*, for Distinguishing between Acute and Chronic Infections in Pregnant Women," Clinical and Diagnostic Laboratory Immunology, vol. 11, No. 6, Nov. 2004, pp. 1016-1021.

Golkar, Majid, et al.; "Evaluation of protective effect of recombinant dense granule antigens GRA2 and GRA6 formulated in monophosphoryl lipid A (MPL) adjuvant against Toxoplasma chronic infection in mice," Vaccine, 22;25(21), May 2007, pp. 4301-4311.

Golkar, Majid, et al.; "The dense granule protein GRA2, a new marker for the serodiagnosis of acute *Toxoplasma* infection: comparison of sera collected in both France and Iran from pregnant women," Diagnostic Microbiology and Infectious Disease, 58(4), Aug. 2007, pp. 419-426.

Golkar, Majid, et al.; "Serodiagnosis of recently acquired *Toxoplasma gondii* infection in pregnant women using enzyme-linked immunosorbent assays with a recombinant dense granule GRA6 protein," Diagnostic Microbiology and Infectious Disease, 61(1), May 2008, pp. 31-39.

Holec-Gasior Lucyna, et al.; "GRA2 and ROP1 Recombinant Antigens as Potential Markers for Detection of *Toxoplasma gondii*-Specific Immunoglobulin G in Humans with Acute Toxoplasmosis," Clinical and Vaccine Immunology, vol. 16, No. 4, Apr. 2009, pp. 510-514.

Jones, Jeffrey L., et al; "*Toxoplasma gondii* Infection in the United States, 1999-2004, Decline from the Prior Decade," American Journal of Tropical Medicine and Hygiene, vol. 77, No. 3, Sep. 2007, pp. 405-410.

(Continued)

*Primary Examiner* — Brian J Gangle
(74) *Attorney, Agent, or Firm* — Harness, Dickey & Pierce, P.L.C.

(57) ABSTRACT

The present disclosure relates to a method for identifying the presence or absence of anti-*Toxoplasma gondii* antibodies in a human or animal serum, including placing the previously drawn serum in contact with antigens capable of binding with the anti-*Toxoplasma gondii* antibodies, and the observation of a bond or of an absence of a bond of antibodies with the antigens, and a combination of two recombinant GRA2 and GRA6 proteins. In particular, the antigens are attached to a support, in particular an ELISA plate. This test is preferably carried out as a supplement to another test for diagnosing toxoplasmosis.

10 Claims, 22 Drawing Sheets

(56) References Cited

OTHER PUBLICATIONS

Kotresha, Dupadahalli, et al.; "Recombinant proteins in the diagnosis of toxoplasmosis," APMIS, vol. 118(8), Aug. 2010, pp. 529-542.

Kusbeci, Ozge Yilmaz, et al.; "Could *Toxoplasma gondii* Have any Role in Alzheimer Disease?" Alzheimer Disease & Associated Disorders, vol. 25, No. 1, Jan.-Mar. 2011, pp. 1-3.

Lecordier, Laurence, et al.; "Molecular structure of a *Toxoplasma gondii* dense granule antigen (GRA 5) associated with the parasitophorous vacuole membrane," Molecular and Biochemical Parasitology, vol. 59, Issue 1, May 1993, pp. 143-153.

Lopez, Adriana, et al.; "Preventing Congenital Toxoplasmosis," MMWR Recomm Rep., 49(RR-2), Mar. 31, 2000, pp. 3159-3168.

Mercier, Corinne, et al.; "Molecular characterization of a dense granule antigen (Gra 2) associated with the network of the parasitophorous vacuole in *Toxoplasma gondii*," Molecular and Biochemical Parasitology, vol. 58, Issue 1, Mar. 1993, pp. 71-82.

Miman, Ozlem, et al.; "The probable relation between *Toxoplasma gondii* and Parkinson's disease," Neuroscience Letters, 475, 2010, pp. 129-131.

Montoya, Jose G., et al.; "Management of *Toxoplasma gondii* Infection during Pregnancy," Clinical Infectious Diseases, 47 (4), Jul. 11, 2008, pp. 554-566.

Pappas, Georgios, et al.; "Toxoplasmosis snapshots: Global status of *Toxoplasma gondii* seroprevalence and implications for pregnancy and congenital toxoplasmosis," International Journal for Parasitology, 39(12), 2009, pp. 1385-1394.

Pedersen, Marianne Giørtz, et al.; "*Toxoplasma* Infection and Later Development of Schizophrenia in Mothers," American Journal of Psychiatry, 168, Aug. 2011, pp. 814-821.

Yolken, R. H., et al.; "Toxoplasma and schizophrenia," Parasite Immunology, vol. 31, Issue 11, Nov. 2009, pp. 706-715.

Lecordier, Laurence, et al.; "Enzyme-Linked Immunosorbent Assays Using the Recombinant Dense Granule Antigens GRA6 and GRA1 of *Toxoplasma gondii* for Detection of Immunoglobulin G Antibodies," Clinical and Diagnostic Laboratory Immunology, vol. 7, No. 4, p. 607-611 (Jul. 2000).

* cited by examiner

Figure 1B

GRA6 Nt (II)

| | 1 | 2 | 3 | 4 | 5 | 6 | 7 | 8 | 9 | 10 |
|---|---|---|---|---|---|---|---|---|---|---|
| 0 | 0.006 | -0.028 | -0.014 | -0.064 | -0.016 | -0.035 | -0.090 | 0.014 | 0.028 | -0.006 |
| 1 | 0.013 | -0.012 | 0.002 | -0.002 | 0.001 | 0.043 | 0.030 | 0.035 | -0.032 | -0.011 |
| 2 | -0.040 | -0.078 | -0.017 | 0.024 | -0.063 | -0.043 | 0.014 | -0.047 | -0.003 | -0.033 |
| 3 | -0.034 | -0.016 | 0.098 | 0.057 | 0.055 | 0.005 | -0.013 | 0.045 | -0.032 | 0.016 |
| 4 | 0.000 | -0.030 | 0.005 | 0.034 | 0.003 | -0.070 | -0.005 | 0.103 | -0.082 | 0.002 |
| 5 | -0.011 | -0.081 | 0.027 | -0.103 | 0.122 | 0.199 | 0.085 | 0.035 | -0.009 | 0.094 |
| 6 | 0.043 | 0.077 | 0.018 | 0.139 | 0.050 | 0.048 | 0.033 | 0.123 | 0.095 | 0.055 |
| 7 | 0.060 | -0.067 | 0.024 | 0.059 | -0.242 | 0.093 | -0.149 | -0.004 | 0.013 | -0.037 |
| 8 | 0.010 | 0.164 | -0.018 | 0.107 | 0.087 | 0.086 | 0.099 | 0.227 | 0.112 | 0.042 |
| 9 | -0.015 | -0.097 | 0.088 | -0.100 | 0.266 | 0.107 | 0.003 | 0.082 | 0.057 | -0.024 |
| 10 | -0.047 | -0.048 | -0.032 | -0.006 | -0.104 | -0.043 | 0.151 | -0.054 | -0.094 | -0.033 |
| 11 | -0.124 | -0.030 | 0.015 | 0.452 | -0.043 | 0.031 | -0.025 | -0.008 | -0.081 | 0.001 |
| 12 | -0.818 | -0.168 | -0.036 | -0.071 | -0.036 | -0.065 | -0.044 | -0.076 | -0.088 | -0.029 |
| 13 | -0.075 | -0.039 | -0.060 | 0.271 | -0.033 | 0.000 | -0.153 | -0.005 | -0.198 | -0.205 |
| 14 | -0.476 | -0.172 | -0.020 | -0.069 | -0.170 | -0.093 | -0.063 | -0.076 | -0.095 | -0.036 |
| 15 | -0.050 | 0.127 | 0.078 | 0.054 | 0.080 | 0.025 | -0.022 | 0.298 | -0.036 | -0.026 |
| 16 | 0.024 | -0.037 | -0.047 | -0.030 | -0.086 | 0.103 | 0.015 | -0.036 | 0.073 | 0.033 |
| 17 | 0.101 | 0.095 | 0.068 | 0.093 | 0.091 | 0.185 | 0.291 | 0.063 | 0.360 | 0.044 |
| 18 | 0.116 | 0.020 | 0.117 | 0.039 | 0.022 | 0.132 | 0.096 | 0.076 | 0.101 | 0.051 |
| 19 | 0.134 | 0.044 | 0.101 | 0.077 | 0.066 | 0.070 | 0.071 | 0.045 | 0.141 | 0.078 |
| 20 | -0.063 | -0.035 | 0.166 | 0.077 | -0.059 | 0.014 | -0.011 | -0.085 | -0.023 | 0.162 |
| 21 | 0.071 | 0.090 | 0.100 | 0.084 | 0.254 | 0.040 | 0.343 | 0.296 | 0.016 | -0.004 |
| 22 | 0.017 | 0.051 | 0.264 | 0.376 | 0.101 | 0.097 | 0.166 | 0.838 | 0.070 | |
| 23 | 0.283 | 0.281 | 0.302 | 0.177 | 0.247 | 0.580 | 0.855 | 0.760 | 0.757 | |
| 24 | 0.608 | 0.830 | | 0.264 | | | 0.425 | 0.114 | 0.222 | 0.350 |
| 25 | 0.172 | 0.098 | -0.181 | -0.210 | 0.176 | -0.046 | -0.096 | | 0.362 | |
| Mean | | | | | | | 0.058 | | | |
| SD | | | | | | | 0.182 | | | |
| Mean + 2 SD | | | | | | | 0.422 | | | |
| Mean + 3 SD | | | | | | | 0.604 | | | |

Figure 3 A

| SC | Patient | ELISA IgG Vidas | IgG IFI | ELISA IgM Vidas | IgM IFI | ISAGA IgM | ELISA IgG GRA2 (II) | ELISA IgG GRA6 Nt (II) | ELISA IgG G2 + G6 Nt (II) |
|---|---|---|---|---|---|---|---|---|---|
| 0-1M | 1 | 2 | | | 1/20 | | 1.205 | 0.574 | 1.422 |
| | 2 | | | | 0 | | 0.612 | 0.536 | 1.301 |
| | 3 | 0 | | | 1/80 | | 0.200 | 1.027 | 0.850 |
| | 4 | 4 | | | 1/80 | | 0.316 | 0.840 | 1.016 |
| | 5 | 0 | 0 | | 1/20 | | 0.255 | 0.664 | 0.550 |
| | 6 | 0 | 0 | | 1/80 | | 0.254 | 0.902 | 0.800 |
| | 7 | | | | 1/80 | | 0.878 | 1.247 | 2.081 |
| | 8 | 2 | | | 1/80 | | 0.190 | 0.295 | 0.699 |
| | 9 | 2 | | | 1/160 | | 0.956 | 0.702 | 1.370 |
| | 10 | | | | 1/80 | | 0.665 | 0.734 | 0.871 |
| | 11 | 0 | | | 1/20 | | 0.025 | 0.403 | 0.764 |
| | 12 | 7 | | | 1/160 | | 0.406 | 0.759 | 0.822 |
| | 13 | 6 | | | 1/160 | | 1.807 | 1.332 | 1.864 |
| | 14 | 0 | | | 0 | | 0.528 | 1.052 | 1.267 |
| | 15 | 4 | | | 1/40 | | 0.095 | 0.868 | 0.557 |
| | 16 | | | | 1/160 | | 1.479 | 1.552 | 2.376 |
| | 17 | | | | | | | | |
| | 18 | | | | 0 | | 0.881 | 2.273 | 2.040 |
| 1-2M | 19 | | | | 0 | | 1.735 | 1.922 | 0.755 |
| | 20 | 5 | | | 1/20 | | 0.283 | 0.550 | 0.658 |
| | 21 | | | | 1/160 | | 0.847 | 1.528 | 1.371 |
| | 22 | 3 | | | 1/80 | | 0.491 | 1.298 | 1.399 |
| | 23 | | | | 1/160 | | 0.495 | 0.964 | 1.053 |
| | 24 | | | | 1/160 | | 1.496 | 1.912 | 1.462 |
| | 25 | | | | 1/160 | | 1.682 | 1.241 | 1.812 |
| | 26 | | | | 1/80 | | 0.290 | 1.619 | 1.563 |
| | 27 | 3 | | | 1/20 | | 0.635 | 0.970 | 0.974 |
| | 28 | 2 | | | 0 | | 0.315 | 0.519 | 0.663 |
| | 29 | | | | 1/80 | | 1.524 | 1.863 | 1.664 |

Figure 3 B

| | Patient | ELISA IgG Vidas | IgG IFI | ELISA IgM Vidas | IgM IFI | ISAGA IgM | ELISA IgG GRA2 (II) | ELISA IgG GRA6 Nt (II) | ELISA IgG G2 + G6 Nt (II) |
|---|---|---|---|---|---|---|---|---|---|
| SC | 30 | 35 | 80 | 3.19 | 1/80 | 12 | 0.858 | 1.063 | 1.410 |
|  | 31 | 14 | 160 | 7.42 | 1/320 | 12 | 0.554 | 2.254 | 2.470 |
|  | 32 | 22 | 80 | 4.77 | 1/80 | 12 | 0.801 | 1.869 | 2.323 |
|  | 33 | 69 | 80 | 3.61 | 1/80 | 12 | 0.666 | 1.483 | 2.574 |
|  | 34 | 32 | 8 | 1.33 | 0 | 12 | 0.309 | 0.402 | 1.133 |
|  | 35 | 14 | 8 | 3.31 | 1/40 | 12 | 0.444 | 0.676 | 0.859 |
|  | 36 | 15 | 8 | 1.66 | 0 | 12 | 1.488 | 0.847 | 1.146 |
|  | 37 | 64 | 320 | 3.28 | 1/80 | 10 | -0.024 | 0.129 | 0.463 |
|  | 38 | 94 | 320 | 0.93 | 0 | 12 | 0.094 | 0.392 | 0.609 |
|  | 39 | 20 | 160 | 3.46 | 1/40 | 10 |  |  |  |
|  | 40 | 240 | 320 | 2.41 | 1/40 | 11 | 1.405 | 1.910 | 2.008 |
|  | 41 | 5 | 1280 | 4.36 | 1/80 | 10 | 1.423 | 1.335 | 0.807 |
|  | 42 | 80 | 8 | 3.69 | 1/20 | 12 | 0.099 | 1.033 | 1.047 |
| 2-3M | 43 | 140 | 640 | 1.51 | 0 | 12 | 2.099 | 2.201 | 1.457 |
|  | 44 | 68 | 320 | 0.63 | 1/80 | 12 | 1.518 | 1.796 | 1.933 |
|  | 45 | 61 | 320 | 1.63 | 1/40 | 12 | 0.570 | 1.653 | 1.941 |
|  | 46 | 66 | 320 | 0.67 | 1/80 | 12 | 1.545 | 1.623 | 1.878 |
|  | 47 | 43 | 160 | 1.71 | 1/20 | 9 | 0.551 | 1.514 | 1.723 |
|  | 48 | 230 | 640 | 1.54 | 1/40 | 12 | 2.206 | 1.964 | 2.016 |
| 3-4M | 49 | 41 | 160 | 3.31 | 1/160 | 12 | 0.321 | 0.964 | 1.170 |
|  | 50 | 43 | 80 | 0.55 | 1/40 | 9 | 0.149 | 1.276 | 0.698 |
|  | 51 | 138 | 320 | 1.19 | 1/40 | 10 | 0.987 | 2.598 | 2.571 |
|  | 52 | 196 | 320 | 3.53 | 1/80 | 12 |  |  |  |
|  | 53 | 74 | 320 | 0.78 | 1/20 | 8 |  |  |  |
|  | 54 | 56 | 80 | 0.29 | 0 | 3 | 0.162 | 0.622 | 0.787 |
|  | 55 | 141 | 640 | 2.36 | 1/40 | 10 | 1.774 | 2.309 | 1.595 |
|  | 56 | 225 | 640 | 1.07 | 0 | 11 | 0.256 | 2.089 | 1.712 |
|  | 57 | 30 | 8 | 0.55 | 0 | 9 | 0.058 | 0.778 | 1.715 |

Figure 3C

| SC | Patient | ELISA IgG Vidas | IgG IFI | ELISA IgM Vidas | IgM IFI | ISAGA IgM | ELISA IgG GRA2 (II) | ELISA IgG GRA6 Nt (II) | ELISA IgG G2 + G6 Nt (II) |
|---|---|---|---|---|---|---|---|---|---|
| 4-5M | 58 | 75 | 160 | 2.29 | 0 | 12 | 0.612 | 0.663 | 0.967 |
| | 59 | 76 | 160 | 2.29 | 0 | 12 | 0.989 | 1.178 | 1.800 |
| | 60 | 28 | 160 | 3.34 | 1/20 | 9 | 0.276 | 0.933 | 0.188 |
| | 61 | 211 | 320 | 1.14 | 0 | 12 | 1.890 | 2.420 | 2.392 |
| | 62 | 171 | 1280 | 1.92 | 1/40 | 12 | 1.242 | 2.411 | 2.551 |
| | 63 | 36 | 80 | 0.68 | 0 | 9 | 0.900 | 1.064 | 1.800 |
| | 64 | 190 | 640 | 3.37 | 1/20 | 12 | | | |
| | 65 | 29 | 80 | 1.19 | 0 | 12 | | | |
| | 66 | 139 | 160 | 1.06 | 0 | 12 | | | |
| | 67 | 43 | 80 | 1.53 | 0 | 12 | 0.098 | 2.530 | 1.751 |
| | 68 | 149 | 160 | 1.83 | 0 | 12 | 0.847 | 1.206 | 1.663 |
| 5-6M | 69 | 70 | 160 | 2.23 | 0 | 12 | 0.989 | 1.221 | 2.171 |
| | 70 | 38 | 80 | 0.44 | 0 | 11 | 0.397 | 0.589 | 0.585 |
| | 71 | 54 | 80 | 0.67 | 0 | 1 | 0.534 | 0.935 | 1.427 |
| | 72 | 226 | 640 | 1.1 | 1/40 | 9 | 0.693 | 1.855 | 2.188 |
| | 73 | 73 | 160 | 2.2 | 0 | 7 | 1.872 | 0.764 | 1.465 |
| 6-7M | 74 | 155 | 160 | 1.05 | 0 | 11 | 0.719 | 0.694 | 1.975 |
| | 75 | 160 | 320 | 3.29 | 1/40 | 10 | 0.378 | 1.290 | 1.446 |
| | 76 | 16 | 160 | 0.13 | 0 | 6 | 0.150 | 0.408 | 0.415 |
| | 77 | 90 | 320 | 0.64 | 0 | 9 | 0.247 | 0.466 | 0.538 |
| | 78 | 23 | 8 | 0.65 | 0 | 12 | | | |
| | 79 | 3 | 8 | 0.29 | 0 | 6 | 0.340 | 0.651 | 0.706 |
| 7-8M | 80 | 19 | 8 | 1.38 | 0 | 6 | 0.665 | 1.319 | 1.563 |
| | 81 | 7 | 8 | 0.43 | 0 | 3 | 0.117 | 0.199 | 0.953 |
| | 82 | 18 | 8 | 0.17 | 0 | 11 | 0.672 | 0.300 | 0.666 |
| | 83 | 47 | 160 | 1.1 | 0 | 11 | 0.303 | 0.779 | 0.957 |
| | 84 | 14 | 8 | 0.58 | 0 | 9 | 0.698 | 1.459 | 2.039 |
| | 85 | 72 | 320 | 1.06 | 0 | 9 | 0.363 | 1.793 | 1.916 |

Figure 3 D

| | Patient | ELISA IgG Vidas | IgG IFI | ELISA IgM Vidas | IgM IFI | ISAGA IgM | ELISA IgG GRA2 (II) | ELISA IgG GRA6 Nt (II) | ELISA IgG G2 + G6 Nt (II) |
|---|---|---|---|---|---|---|---|---|---|
| SC | 86 | | | | | | | | 1.558 |
| | 87 | | | | | | | | |
| | 88 | | | | | 13 | 0.945 | 1.134 | 1.309 |
| | 89 | | | | | 9 | 1.247 | 0.933 | 0.987 |
| | 90 | | | 0.32 | 3/40 | 12 | 0.167 | 0.386 | 1.888 |
| | 91 | | | | | 6 | 0.219 | 2.089 | 1.312 |
| | 92 | | | 0.43 | | 6 | 1.631 | 0.999 | 0.738 |
| | | | | | | | 0.286 | 0.646 | |
| 8-9M | 93 | | | | | 9 | 0.519 | 1.138 | 0.947 |
| | 94 | | | | 1/20 | 10 | 0.792 | 0.962 | 2.017 |
| | 95 | | | | | 9 | 0.342 | 0.898 | 0.948 |
| | 96 | | | | 1/20 | 10 | 0.424 | 1.074 | 1.324 |
| | 97 | | | | | 12 | 0.595 | 1.454 | 1.512 |
| | 98 | | | | | 12 | 1.364 | 1.198 | 1.513 |
| | 99 | | | | | 11 | 0.084 | 0.653 | 0.961 |
| | 100 | | | | | 9 | 0.851 | 1.333 | 1.948 |
| | 101 | | | | | 12 | 0.544 | 1.936 | 1.720 |
| >9M | 102 | | | | 1/40 | 12 | 1.399 | 1.814 | 2.112 |
| | 103 | | | 0.64 | | 9 | 1.140 | 2.516 | 2.528 |
| | 104 | | | | | 12 | 0.532 | 1.602 | 1.824 |
| | 105 | | | | | 10 | 0.472 | 0.984 | 1.540 |
| | 106 | | | | | 13 | 0.919 | 0.806 | 1.630 |
| | 107 | | | | | 12 | -0.073 | 1.457 | 1.198 |
| | 108 | | | | | 12 | 0.750 | 1.081 | 0.610 |
| | 109 | | | | 1/20 | 9 | 1.254 | 0.890 | 2.403 |
| | 110 | | | 0.41 | | 9 | 0.537 | 0.664 | 1.616 |
| | 111 | | | | 1/40 | 12 | 0.446 | 0.771 | 1.259 |
| | 112 | | | 0.29 | | 11 | 0.469 | 1.338 | 1.268 |
| | 113 | | | 0.49 | | 9 | 0.209 | 1.112 | 1.129 |
| | 114 | | | 0.57 | | 9 | -0.027 | 0.984 | 1.302 |

Figure 3E

| SC | Patient | ELISA IgG Vidas | IgG IFI | ELISA IgM Vidas | IgM IFI | ISAGA IgM | ELISA IgG GRA2 (II) | ELISA IgG GRA6 Nt (II) | ELISA IgG G2 + G6 Nt (II) |
|---|---|---|---|---|---|---|---|---|---|
| | 115 | >300 | 640 | 1.42 | 0 | 12 | 0.509 | 1.564 | 1.951 |
| | 116 | 17 | 8 | 0.53 | 0 | 9 | 0.354 | 0.416 | 0.686 |
| | 117 | 188 | 80 | 0.33 | 0 | 9 | 1.801 | 2.086 | 2.137 |
| | 118 | 44 | 320 | 1.96 | 1/40 | 12 | 0.065 | 0.938 | 0.881 |
| | 119 | 45 | 80 | 3.42 | 1/40 | 12 | 0.753 | 1.751 | 1.680 |
| | 120 | 77 | 160 | 2.9 | 1/40 | 12 | 0.182 | 1.687 | 1.866 |
| | 121 | 45 | 80 | 3.27 | 1/20 | 12 | 0.007 | 1.664 | 2.150 |
| | 122 | 246 | 320 | 1.04 | 0 | 9 | 0.374 | 2.278 | 1.350 |
| | 123 | >300 | 640 | 1.23 | 0 | 10 | 0.635 | 1.598 | 1.452 |
| | 124 | 47 | 80 | 2.19 | 0 | 12 | 0.532 | 0.233 | 1.008 |
| | 125 | 150 | 640 | 2.25 | 1/40 | 12 | 0.866 | 1.739 | 2.247 |
| | 126 | 189 | 80 | 2.82 | 1/20 | 12 | 1.942 | 1.714 | 2.060 |
| | 127 | 101 | 160 | 2.47 | 1/40 | 12 | 1.423 | 1.436 | 1.924 |
| | 128 | >300 | 320 | 2.86 | 0 | 12 | 1.493 | 1.774 | 1.906 |
| | 129 | >300 | 1280 | 0.64 | 0 | 9 | 1.445 | 1.816 | 1.903 |
| | 130 | >300 | 320 | 1.43 | 0 | 12 | 1.046 | 1.895 | 1.827 |
| | 131 | 212 | 160 | 2.2 | 1/20 | 12 | 0.972 | 1.150 | 1.671 |

|  |  |  |  |  |  |  | Diagnosis |  |  | GRA2 + GRA6 Nt |
|---|---|---|---|---|---|---|---|---|---|---|
| Patient | Serum | ELFA IgG Vidas | IFI IgG | ELISA IgM Vidas | IFI IgM | ISAGA IgM | (IgM+IgG) | GRA2 (II) | GRA6 Nt (II) | (II) 50/50 |
| 7 | 22 | 0 | 0 | 0.02 | 0 |  | neg | 0.949 | 0.130 | 0.203 |
|  | 23 | 1 | 8 | 1.93 | 1/40 |  | pos | 1.275 | 1.260 | 1.336 |
|  | 24 | 21 | 160 | 2.74 | 1/40 |  | pos | 1.857 | 1.590 | 0.798 |
|  | 25 | 104 | 640 | 3.41 | 1/40 |  | pos | 2.081 | 1.531 | 1.730 |
|  | 26 | 205 | 1280 | 1.68 | 0 | 12 | pos | 1.613 | 1.284 | 1.572 |
| 8 | 27 | 0 | 0 | 0.07 | 0 | 3 | neg | 0.414 | 0.266 | -0.021 |
|  | 28 | 4 | 80 | 2.97 | 1/80 | 10 | pos | 1.703 | 1.674 | 1.075 |
|  | 29 | 23 | 160 | 2.61 | 1/40 | 12 | pos | 1.332 | 1.360 | 1.106 |
|  | 30 | 73 | 80 | 1.66 | 0 | 11 | pos | 0.391 | 1.240 | 0.282 |
| 9 | 31 | 0 | 0 | 0.08 | 0 | 0 | neg | 0.009 | 0.500 | 0.085 |
|  | 32 | 0 | 8 | 7.93 | 1/640 | 10 | pos | 0.276 | 1.256 | 0.721 |
|  | 33 | 0 | 8 | 7.45 | 1/640 | 11 | pos | 0.451 | 1.610 | 0.884 |
| 10 | 34 | 0 | 0 | 0.07 | 0 | 0 | neg | 0.024 | 0.319 | 0.025 |
|  | 35 | 6 | 160 | 7.64 | 1/320 | 10 | pos | 1.977 | 1.975 | 2.040 |
|  | 36 | 35 | 320 | 8.53 | 1/640 | 12 | pos | 1.055 | 2.102 | 2.169 |
|  | 37 | 203 | 160 | 2.9 | 0 | 12 | pos | 0.997 | 1.650 | 0.985 |
| 11 | 38 | 0 | 0 | 0.11 | 0 | 0 | neg | 0.134 | 0.993 | 0.151 |
|  | 39 | 5 | 160 | 8.52 | 1/320 | 13 | pos | 0.945 | 2.064 | 2.245 |
|  | 40 | 22 | 320 | 8.53 | 1/320 | 12 | pos | 1.142 | 2.208 | 2.350 |
| 12 | 41 | 0 | 0 | 0.03 | 0 | 0 | neg | 0.177 | 0.128 | 0.100 |
|  | 42 | 0 | 0 | 3.4 | 0 | 12 | pos | 0.197 | 0.214 | 0.001 |
|  | 43 | 0 | 0 | 4.72 | 1/20 | 12 | pos | 0.261 | 0.194 | 0.030 |
|  | 44 | 85 | 320 | 5.93 | 1/40 | 12 | pos | 1.056 | 1.632 | 1.829 |
|  | 45 | 167 | 320 | 4.14 | 0 | 12 | pos | 1.242 | 1.792 | 2.029 |

Figure 4 C

| Patient | Serum | ELFA IgG Vidas | IFI IgG | ELISA IgM Vidas | IFI IgM | ISAGA IgM | Diagnosis (IgM+IgG) | GRA2 (II) | GRA6 Nt (II) | GRA2 + GRA6 Nt (II) 50/50 |
|---|---|---|---|---|---|---|---|---|---|---|
| 13 | 46 | 0 | 0 | 0.06 | 0 | 0 | neg | 0.064 | 0.058 | 0.195 |
|  | 47 |  |  |  |  |  | pos | 1.179 | 1.515 | 2.203 |
|  | 48 |  |  |  | 1/20 |  | pos | 1.052 | 1.318 | 1.499 |
|  | 49 |  |  |  | 0 |  | pos | 0.246 | 0.667 | 0.910 |
| 14 | 50 | 0 | 0 | 0.04 | 0 | 0 | neg | 0.035 | 0.024 | 0.285 |
|  | 51 | 275 |  |  |  |  | pos | 1.211 | 1.734 | 2.268 |
|  | 52 |  |  |  |  |  | pos | 1.604 | 1.906 | 1.890 |
|  | 53 | 77 |  |  |  |  | pos | 0.253 | 0.792 | 0.626 |
| 15 | 54 | 0 | 0 | 0.06 | 0 | 0 | neg | 0.524 | 0.038 | 0.093 |
|  | 55 | 0 | 0 |  | 1/20 |  | pos | 0.605 | 0.141 | 0.775 |
|  | 56 | 3 |  |  |  |  | pos | 1.181 | 0.585 | 1.668 |
|  | 57 |  |  |  |  |  | pos | 0.211 | 0.979 | 0.510 |
| 16 | 58 | 0 | 0 | 0.08 | 0 | 3 | neg | 1.439 | 0.573 | 0.390 |
|  | 59 |  |  |  | 0 |  | pos | 1.874 | 1.708 | 1.840 |
|  | 60 |  |  |  | 0 |  | pos | 1.734 | 1.614 | 1.401 |
|  | 61 |  |  |  | 0 |  | pos | 0.964 | 1.080 | 0.806 |
| 17 | 62 | 0 | 0 | 0.08 | 0 | 0 | neg | 0.001 | 0.046 | 0.050 |
|  | 63 | 0 | 0 |  | 0 |  | pos | 0.030 | 0.216 | 0.414 |
|  | 64 |  |  | 0.45 | 0 |  | pos | 0.052 | 0.313 | 0.682 |
| 18 | 65 | 0 | 0 |  |  |  | pos | 0.050 | 0.234 | 0.298 |
|  | 66 | 4 |  |  |  |  | pos | 0.236 | 0.682 | 1.006 |
|  | 67 |  |  |  |  |  | pos | 0.349 | 0.588 | 0.554 |

Figure 4 D

| Patient | Serum | ELFA IgG Vidas | IFI IgG | ELISA IgM Vidas | IFI IgM | ISAGA IgM | Diagnosis (IgM+IgG) | GRA2 (II) | GRA6 Nt (II) | GRA2 + GRA6 Nt (II) 50/50 |
|---|---|---|---|---|---|---|---|---|---|---|
| 19 | 68 | 0 | 0 | 0.05 | 0 | 0 | neg | -0.042 | 0.182 | 0.063 |
|  | 69 | 0 | 0 |  | 0 |  | pos | 0.049 | 0.128 | 0.341 |
|  | 70 | 2 |  |  | 0 |  | pos | 0.408 | 0.230 | 0.778 |
|  | 71 |  |  |  |  |  | pos | 0.765 | 1.537 | 0.746 |
|  | 72 |  |  |  | 0 |  | pos | 2.378 | 1.863 | 1.511 |
| 20 | 73 | 0 | 0 | 0.09 | 0 | 0 | neg | 0.155 | 0.124 | 0.288 |
|  | 74 | 0 | 0 |  | 0 |  | pos | 0.190 | 0.178 | 0.783 |
|  | 75 | 0 |  |  | 0 |  | pos | 0.109 | 0.641 | 0.582 |
|  | 76 |  |  | 0.52 |  |  | pos | 0.281 |  | 0.390 |
| 21 | 77 | 0 | 0 | 0.1 | 0 | 3 | neg | 0.590 |  | 0.451 |
|  | 78 |  |  |  |  |  | pos | 0.922 |  | 1.554 |
|  | 79 |  |  |  | 1/20 |  | pos | 0.049 | 0.349 | 0.183 |
| 22 | 80 | 0 | 0 | 0.05 | 0 | 3 | neg | 0.236 |  | 1.038 |
|  | 81 | 0 | 0 |  | 0 |  | pos | 0.436 | 0.783 | 0.785 |
|  | 82 |  |  |  |  |  | pos | 1.794 |  | 2.195 |
|  | 83 |  |  |  | 0 |  | pos | 0.997 |  | 1.498 |
| 23 | 84 | 0 | 0 | 0.3 | 0 |  | neg | 1.041 | -0.151 | 0.800 |
|  | 85 | 1 |  |  |  |  | pos | 1.764 |  | 2.265 |
|  | 86 |  |  |  |  |  | pos | 2.392 | 2.520 | 2.331 |
|  | 87 |  |  |  | 0 |  | pos | 1.776 |  | 0.852 |
| 24 | 88 | 0 | 0 | 0.07 | 0 | 0 | neg | 0.314 | 0.341 | 0.190 |
|  | 89 | 0 |  |  | 1/20 |  | pos | 1.610 | 1.227 | 0.706 |
|  | 90 | 3 |  |  |  |  | pos | 2.594 | 1.314 | 1.397 |

Figure 4E

| Patient | Serum | ELFA IgG Vidas | IFI IgG | ELISA IgM Vidas | IFI IgM | ISAGA IgM | Diagnosis (IgM+IgG) | GRA2 (II) | GRA6 Nt (II) | GRA2 + GRA6 Nt (II) 50/50 |
|---|---|---|---|---|---|---|---|---|---|---|
| 25 | 91 | 29 | 160 | 2.46 | 1/160 | 12 | pos | 2.155 | 2.242 | 1.465 |
|  | 92 | 0 | 0 | 0.04 | 0 | 0 | neg | 0.413 | 0.719 | 0.146 |
|  | 93 | 52 | 320 | 3.52 | 1/160 | 12 | pos | 2.424 | 2.669 | 2.488 |
|  | 94 | 203 | 320 | 0.67 | 0 | 14 | pos | 1.863 | 1.867 | 2.003 |
| 26 | 95 | 0 | 0 | 0.13 | 0 | 0 | neg | 0.502 | 1.307 | 0.031 |
|  | 96 | 4 | 6 | 0.48 | 1/160 | 12 | pos | 2.043 | 2.363 | 2.041 |
|  | 97 | 33 | 80 | 1.78 | 0 | 12 | pos | 1.711 | 0.359 | 1.396 |
| 27 | 98 | 0 | 0 | 0.06 | 0 | 0 | neg | 0.127 | 1.072 | 0.497 |
|  | 99 | 85 | 320 | 0.18 | 1/160 | 13 | pos | 1.960 | 2.295 | 1.957 |
|  | 100 | 144 | 320 | 0.89 | 1/160 | 14 | pos | 1.805 | 2.309 | 0.918 |
| 28 | 101 | 0 | 0 | 0.1 | 0 | 0 | neg | 0.099 | 0.558 | 1.165 |
|  | 102 | 66 | 160 | 0.83 | 1/160 | 12 | pos | 1.356 | 1.871 | 2.710 |
|  | 103 | 45 | 80 | 3.77 | 1/20 | 14 | pos | 0.337 | 1.227 | 1.638 |
| 29 | 104 | 0 | 0 | 0.03 | 0 | 0 | neg | 0.169 | 0.036 | 0.262 |
|  | 105 | 1 | 0 | 3.2 | 1/160 | 13 | pos | 1.353 | 1.555 | 2.135 |
|  | 106 | 108 | 320 | 1.66 | 1/160 | 13 | pos | 1.374 | 1.802 | 2.080 |
| 30 | 107 | 0 | 0 | 0.03 | 0 | 0 | neg | 0.310 | 0.153 | 0.281 |
|  | 108 | 0 | 8 | 2.64 | 1/40 | 12 | pos | 0.416 | 0.509 | 0.836 |
|  | 109 | 2 | 4 | 3.3 | 1/60 | 13 | pos | 0.675 | 0.867 | 1.183 |
|  | 110 | 46 | 80 | 4.03 | 1/160 | 13 | pos | 1.320 | 0.863 | 1.714 |
|  | 111 | 74 | 320 | 1.76 | 1/20 | 9 | pos | 1.337 | 2.125 | 2.557 |
| 31 | 112 | 0 | 0 | 0.25 | 0 | 0 | neg | 0.277 | 0.471 | 0.553 |

Figure 4 F

| Patient | Serum | ELFA IgG Vidas | IFI IgG | ELISA IgM Vidas | IFI IgM | ISAGA IgM | Diagnosis (IgM+IgG) | GRA2 (II) | GRA6 Nt (II) | GRA2 + GRA6 Nt (II) 50/50 |
|---|---|---|---|---|---|---|---|---|---|---|
|  | 113 | 2 | 8 | 5.52 | 1/80 | 12 | pos | 0.862 | 1.697 | 1.787 |
|  | 114 | 12 | 80 | 5.26 | 1/80 | 12 | pos | 1.209 | 2.171 | 2.084 |
|  | 115 | 30 | 80 | 1.11 | 0 | 11 | pos | 0.268 | 0.978 | 0.927 |
| 32 | 116 | 0 | 0 | 0.03 | 0 | 0 | neg | 0.074 | 0.263 | 0.241 |
|  | 117 | 0 | 8 | 0.82 | 0 | 12 | pos | 0.118 | 0.385 | 0.678 |
|  | 118 | 71 | 160 | 0.97 | 0 | 12 | pos | 0.151 | 0.732 | 0.805 |
|  | 119 | 94 | 320 | 0.94 | 0 | 12 | pos | 0.133 | 0.735 | 0.700 |
|  | 120 | 70 | 160 | 0.52 | 0 | 12 | pos | 0.149 | 0.475 | 0.377 |

Figure 5 A

| Patient | Serum | VIDAS IgG | IFI IgG | Vidas IgM | IFI IgM | ISAGA | Diagnosis | GRA2 (II) | GRA6 Nt (II) | GRA2 + GRA6 Nt(II) 50/50 |
|---|---|---|---|---|---|---|---|---|---|---|
| 1 | 1 | 33 | 80 | 0.02 | 0 | 0 | | 1.328 | 2.012 | 2.341 |
|  | 2 | 7 | 8 | 0.03 | 0 | 0 | | 0.952 | 1.617 | 1.740 |
|  | 3 | 46 | 100 | 0.54 | 0 | 3 | TC+ | 2.256 | 2.305 | 2.693 |
|  | 4 | 36 | 640 | 0.31 | 0 | 0 | | 2.276 | 1.856 | 2.446 |
|  | 5 | 27 | 80 | 0.11 | 0 | 0 | | 1.336 | 1.879 | 2.377 |
|  | 6 | 22 | 8 | 0.03 | 0 | 0 | | 0.762 | 0.797 | 1.514 |
|  | 7 | 20 | 8 | 0.04 | 0 | 0 | | 0.711 | 0.866 | 1.415 |
|  | 8 | 28 | 8 | 0.03 | 0 | 0 | | 1.043 | 0.603 | 1.304 |
|  | 9 | 22 | 8 | 0.05 | 0 | 0 | | 0.967 | 0.765 | 0.775 |
| 2 | 10 | 54 | 160 | 0.05 | 0 | 0 | | 0.859 | 1.948 | 2.203 |
|  | 11 | 17 | 80 | 0.06 | 0 | 0 | | 1.828 | 1.363 | 1.740 |
|  | 12 | 20 | 8 | 0.03 | 0 | 0 | | 0.995 | 1.052 | 1.641 |
|  | 13 | 14 | 8 | 0.04 | 0 | 0 | | 0.858 | 0.359 | 0.627 |
|  | 14 | 10 | 0 | 0.05 | 0 | 0 | TC+ | 1.057 | 1.061 | 1.382 |
|  | 15 | >300 | 640 | 0.22 | 0 | 0 | | 2.177 | 1.111 | 2.149 |
|  | 16 | >300 | 320 | 0.14 | 0 | 0 | | 1.532 | 0.989 | 2.082 |
| 3 | 17 | 9 | 160 | 0.06 | 0 | 0 | TC- | 1.084 | 1.454 | 1.373 |
|  | 18 | 10 | 8 | 0.02 | 0 | 0 | | 0.233 | 0.460 | 0.266 |
|  | 19 | 7 | 8 | 0.02 | 0 | 0 | | 0.171 | 0.355 | 0.278 |
| | 3 : a later sample would have been of interest | | | | | | | | | |
| 4 | 20 | 2 | 8 | 0.22 | 0 | 0 | TC- | 0.084 | 0.197 | 0.093 |
|  | 21 | 0 | 0 | 0.08 | 0 | 0 | | 0.018 | 0.076 | 0.133 |
|  | 22 | 0 | 0 | 0.03 | 0 | 0 | | 0.012 | 0.090 | 0.065 |
| 5 | 23 | >300 | 1280 | 0.13 | 0 | 0 | TC- | 0.365 | 0.793 | 1.274 |
|  | 24 | >300 | 320 | 0.04 | 0 | 0 | | 0.882 | 1.034 | 1.423 |
|  | 25 | 157 | 320 | 0.05 | 0 | 0 | | 0.317 | 0.769 | 0.915 |
|  | 26 | 64 | 8 | 0.01 | 0 | 0 | | 0.210 | 0.347 | 0.476 |

Figure 5 B

| Patient | Serum | VIDAS IgG | IFI IgG | Vidas IgM | IFI IgM | ISAGA | Diagnosis | GRA2 (II) | GRA6 Nt (II) | GRA2 + GRA6 Nt(II) 50/50 |
|---|---|---|---|---|---|---|---|---|---|---|
| 6 | 27 | 7 | 6 | 0.11 | 0 | 0 | | 0.000 | 0.201 | 0.191 |
| | 28 | 1 | 0 | 0.12 | 0 | 0 | | -0.027 | 0.114 | 0.158 |
| | 29 | 0 | 0 | 0.06 | 0 | 0 | | -0.010 | 0.104 | 0.164 |
| | 30 | 107 | 50 | 0.07 | 0 | 0 | TC- | 0.800 | 0.666 | 0.697 |
| | 31 | 36 | 3 | 0.02 | 0 | 0 | | 0.333 | 0.253 | 0.303 |
| | 32 | 0 | 0 | 0.06 | 0 | 0 | | 0.299 | 0.252 | 0.173 |
| 7 | 33 | 88 | 8 | 0.07 | 0 | 0 | TC- | 0.534 | 1.176 | 0.738 |
| | 34 | 7 | 3 | 0.02 | 0 | 0 | | 0.407 | 0.624 | 0.588 |
| | 35 | 1 | 0 | 0.03 | 0 | 0 | | 0.200 | 0.152 | 0.142 |
| | 36 | 0 | 0 | 0.04 | 0 | 0 | | 0.230 | 0.188 | 0.162 |
| | 7 : a later sample would have been of interest | | | | | | | | | |
| 8 | 37 | 26 | 20 | 0.02 | 0 | 0 | TC- | 0.221 | 0.188 | 0.193 |
| | 38 | 0 | 0 | 0.01 | 0 | 0 | | -0.002 | 0.067 | 0.076 |
| | 39 | 0 | 0 | 0.06 | 0 | 0 | | -0.415 | -0.013 | 0.088 |
| 9 | 40 | 120 | 150 | 2.19 | 0 | 12 | TC+ | 0.702 | 2.042 | 2.474 |
| | 41 | 70 | 80 | 0.47 | 0 | 3 | | 0.656 | 2.173 | 2.597 |
| | 42 | 48 | 80 | 0.14 | 0 | 3 | | 0.364 | 1.590 | 1.998 |
| | 43 | 44 | 8 | 0.1 | 0 | 0 | | 0.369 | 0.836 | 1.398 |
| | 44 | 36 | 3 | 0.03 | 0 | 0 | | 0.110 | 0.804 | 0.912 |
| | 45 | 33 | 8 | 0.05 | 0 | 0 | | 0.171 | 0.753 | 0.857 |
| 10 | 46 | 39 | 6 | 1.41 | 0 | 12 | TC+ | 0.126 | 1.186 | 0.698 |
| | 47 | 35 | 6 | 0.14 | 0 | 3 | | 0.205 | 1.388 | 1.460 |
| | 48 | 50 | 3 | 0.04 | 0 | 0 | | -0.006 | 0.855 | 2.243 |
| | 49 | 31 | 3 | 0.01 | 0 | 0 | | 0.090 | 0.616 | 1.121 |
| | 50 | 16 | 3 | 0.03 | 0 | 0 | | 0.101 | 0.342 | 1.748 |
| | 51 | 12 | 0 | 0.08 | 0 | 0 | | 0.038 | 0.191 | 1.847 |

Figure 5 C

| Patient | Serum | VIDAS IgG | IFI IgG | Vidas IgM | IFI IgM | ISAGA | Diagnosis | GRA2 (II) | GRA6 Nt (II) | GRA2 + GRA6 Nt(II) 50/50 |
|---|---|---|---|---|---|---|---|---|---|---|
|  | 52 | 4 | 8 | 0.08 | 0 | 0 |  | 0.090 | 0.025 | 1.579 |
|  | 53 | 4 | 8 | 0.08 | 0 | 0 |  | 0.221 | 0.205 | 1.478 |
|  | 10 : a later sample would have been of interest |  |  |  |  |  |  |  |  |  |
| 11 | 54 | 0 | 0 | 0.12 | 0 | 0 |  | -0.071 | 0.061 | 0.045 |
|  | 55 | 50 | 8 | 0.07 | 0 | 0 |  | 0.071 | 0.822 | 0.851 |
|  | 56 | 65 | 8 | 0.09 | 0 | 0 |  | 0.096 | 0.986 | 0.836 |
|  | 57 | 80 | 8 | 0.17 | 0 | 0 |  | 0.101 | 0.713 | 0.668 |
|  | 58 | 120 | 8 | 0.17 | 0 | 0 | TC+ | 0.263 | 0.395 | 0.568 |
|  | 59 | 200 | 200 | 0.2 | 0 | 3 |  | 0.796 | 0.853 | 1.014 |
|  | 60 | 200 | 320 | 0.24 | 0 | 3 |  | 0.602 | 0.774 | 1.056 |
| 12 | 61 | 200 | 320 | 0.26 | 0 | 0 |  | 0.649 | 1.260 | 1.095 |
|  | 62 | 135 | 320 | 0.06 | 0 | 0 |  | 0.740 | 1.225 | 1.092 |
|  | 63 | 17 | 8 | 0.03 | 0 | 0 | TC- | 0.181 | 0.238 | 0.199 |
|  | 64 | 4 | 8 | 0.05 | 0 | 0 |  | 0.052 | -0.002 | 0.079 |
|  | 65 | 0 | 0 | 0.08 | 0 | 0 |  | 0.042 | -0.015 | -0.030 |
| 13 | 66 | 8 | 8 | 0.05 | 0 | 0 |  | 0.651 | 0.855 | 0.938 |
|  | 67 | 4 | 8 | 0.08 | 0 | 0 | TC- | 0.124 | 0.171 | 0.156 |
|  | 68 | 0 | 0 | 0.09 | 0 | 0 |  | 0.115 | 0.150 | 0.074 |
| 14 | 69 | 160 | 160 | 0.05 | 0 | 0 |  | 0.481 | 2.157 | 1.425 |
|  | 70 | 100 | 160 | 0.03 | 0 | 0 |  | 1.036 | 1.342 | 1.903 |
|  | 71 | 80 | 8 | 0.93 | 0 | 3 |  | 1.423 | 0.942 | 1.771 |
|  | 72 | 30 | 8 | 0.12 | 0 | 0 | TC+ | 0.681 | 0.481 | 0.651 |
|  | 73 | 5 | 0 | 0.09 | 0 | 0 |  | 0.735 | 0.394 | 0.539 |
|  | 74 | 8 | 8 | 0.07 | 0 | 0 |  | 0.663 | 0.894 | 0.671 |
|  | 75 | 2300 | 160 | 0.12 | 0 | 0 |  | 0.892 | 0.797 | 2.141 |
|  | 76 | 140 | 80 | 0.12 | 0 | 0 |  | 0.513 | 0.685 | 0.450 |

Figure 5D

| Patient | Serum | VIDAS IgG | IFI IgG | Vidas IgM | IFI IgM | ISAGA | Diagnosis | GRA2 (II) | GRA6 Nt (II) | GRA2 + GRA6 Nt(II) 50/50 |
|---|---|---|---|---|---|---|---|---|---|---|
| 15 | 77 | 61 | 160 | 0.45 | 0 | 12 |  | 0.613 | 2.252 | 2.107 |
|  | 78 | 21 | 8 | 0.06 | 0 | 0 |  | 0.633 | 1.324 | 1.361 |
|  | 79 | 19 | 8 | 0.06 | 0 | 0 |  | 0.652 | 0.873 | 1.239 |
|  | 80 | 16 | 8 | 0.12 | 0 | 0 | TC+ | 0.860 | 0.564 | 0.965 |
|  | 81 | 19 | 8 | 0.15 | 0 | 0 |  | 0.426 | 0.710 | 0.796 |
|  | 82 | 15 | 8 | 0.16 | 0 | 0 |  | 0.346 | 0.516 | 0.289 |
|  | 83 | >400 | 1280 | 0.33 | 0 | 6 |  | 0.846 | 1.580 | 1.257 |
| 16 | 84 | 3 | 8 | 0.2 | 0 | 0 |  | 0.088 | 0.272 | 0.049 |
|  | 85 | 1 | 0 | 0.06 | 0 | 0 | TC- | 0.020 | -0.004 | 0.038 |
|  | 86 | 0 | 0 | 0.03 | 0 | 0 |  | 0.065 | 0.031 | 0.028 |
| 17 | 87 | >400 | 640 | 0.09 | 0 | 0 |  | 0.664 | 1.525 | 1.672 |
|  | 88 | 112 | 80 | 0.04 | 0 | 0 | TC- | 0.550 | 1.255 | 1.128 |
|  | 89 | 1 | 8 | 0.03 | 0 | 0 |  | 0.444 | 0.342 | 0.444 |
|  | 90 | 0 | 0 | 0.07 | 0 | 0 |  | 0.329 | 0.103 | 0.120 |
| 18 | 91 | >400 | 1280 | 0.23 | 0 | 0 |  | 0.979 | 1.309 | 1.327 |
|  | 92 | 177 | 320 | 0.44 | 0 | 0 | TC+ | 0.750 | 1.280 | 1.170 |
|  | 93 | >400 | 1280 | 0.33 | 0 | 12 |  | 0.816 | 1.096 | 1.020 |
| 19 | 94 | 102 | 320 | 0.41 | 0 | 6 |  | 1.000 | 1.229 | 0.985 |
|  | 95 | 49 | 160 | 0.15 | 0 | 0 |  | 0.201 | 0.939 | 0.641 |
|  | 96 | >400 | 320 | 0.34 | 0 | 12 |  | 0.707 | 0.876 | 0.764 |
|  | 97 | 244 | 640 | 0.08 | 0 | 0 | TC+ | 0.751 | 0.966 | 0.713 |
|  | 98 | 247 | 320 | 0.1 | 0 | 12 |  | 0.606 | 0.763 | 0.690 |
|  | 99 | 120 | 320 | 0.06 | 0 | 0 |  | 0.208 | 0.532 | 0.633 |
|  | 100 | 137 | 80 | 0.07 | 0 | 0 |  | 0.207 | 0.677 | 0.554 |
| 20 | 101 | 125 | 320 | 0.23 | 0 | 0 |  | 0.648 | 1.368 | 1.238 |

Figure 5 E

| Patient Serum | VIDAS IgG | IFI IgG | Vidas IgM | IFI IgM | ISAGA | Diagnosis | GRA2 (II) | GRA6 Nt (II) | GRA6 Nt(II) | GRA2 + GRA6 50/50 |
|---|---|---|---|---|---|---|---|---|---|---|
| 102 | 23 | 8 | 0.05 | 0 | 0 | | 0.121 | 0.531 | | 0.609 |
| 103 | 5 | 8 | 0.05 | 0 | 0 | | -0.026 | 0.129 | | 0.027 |
| 104 | 0 | 8 | 0.05 | 0 | 0 | | 0.099 | -0.133 | | -0.400 |
| 105 | 0 | 0 | 0.05 | 0 | | | 0.000 | -0.466 | | -0.946 |
| 106 | 59 | 160 | 3.52 | 1/40 | 12 | TC+ | 1.673 | 1.577 | | 1.498 |

| | | 3 SD | 2 SD | 3 SD | 2 SD |
|---|---|---|---|---|---|
| GRA2 (II) | chronic | 92/223 (41.25%) | 122/252 (48.41%) | 92/253 (36.36%) | 122/253 (48.22%) |
| | SC dated | 90/102 (88.23%) | 101/110 (91.81%) | 90/120 (75%) | 101/120 (84.16%) |
| | SC sequential | 75/56 (133.92%) | 87/62 (140.32%) | 75/79 (94.93%) | 87/79 (110.12%) |
| | CT | 60/76 (78.94%) | 67/86 (77.90%) | 60/90 (66.66%) | 67/90 (74.44%) |
| | Total | 317/457 (69.36%) | 377/510 (73.92%) | 317/542 (58.42%) | 377/542 (69.55%) |
| GRA6 Nt (II) | chronic | 110/223 (83.45%) | 165/252 (65.47%) | 110/253 (43.47%) | 165/253 (65.21%) |
| | SC dated | 105/102 (102.94%) | 112/110 (101.81%) | 105/120 (87.5%) | 112/120 (93.33%) |
| | SC sequential | 78/56 (139.28%) | 86/62 (138.70%) | 78/79 (98.73%) | 86/79 (108.86%) |
| | CT | 63/76 (82.89%) | 70/86 (81.39%) | 63/90 (70%) | 70/90 (77.77%) |
| | Total | 356/457 (77.90%) | 433/510 (84.90%) | 356/542 (65.62%) | 433/542 (79.88%) |
| GRA2 + GRA6 Nt (II) | chronic | 195/223 (87.44%) | 219/252 (86.90%) | 195/253 (77.07%) | 219/253 (86.56%) |
| | SC dated | 121/102 (118.62%) | 133/110 (110%) | 121/120 (100.83%) | 121/120 (100.83%) |
| | SC sequential | 85/56 (151.78%) | 94/62 (151.61%) | 85/79 (107.59%) | 94/79 (118.98%) |
| | CT | 77/76 (101.31%) | 81/86 (94.18%) | 77/90 (85.55%) | 81/90 (90%) |
| | Total | 478/457 | 515/510 | 478/542 (88.19%) | 515/542 |
| VIDAS IgG | chronic | | | 223/253 (88.14%) | 252/253 (99.60%) |
| | SC dated | | | 102/120 (85%) | 110/120 (91.66%) |
| | SC sequential | | | 56/79 (70.88%) | 62/79 (78.48%) |
| | CT | | | 76/90 (84.44%) | 86/90 (95.55%) |
| | Total | | | 457/543 (84.31%) | 510/542 |

Figure 6

RECOMBINANT GRA ANTIGENS AND THE USE OF SAME FOR EARLY DIAGNOSIS OF TOXOPLASMOSIS

CROSS-REFERENCE TO RELATED APPLICATIONS

This application is a National Phase Entry of International Application No. PCT/EP2013/071578, filed on Oct. 16, 2013, which claims priority to French Patent Application Serial No. 1259850, filed on Oct. 16, 2012, both of which are incorporated by reference herein.

FIELD OF THE INVENTION

The present invention concerns a method for early in vitro diagnosis of infection with toxoplasmosis in humans, and a diagnosis kit.

BACKGROUND

Toxoplasmosis, an infection caused by the protozoan parasite *Toxoplasma gondii*, affects at least one third of the world's human population. There only exists one genus and one species of the parasite *Toxoplasma* but the parasitic isolates are currently classified into 12 haplogroups I to XII. The strains mostly encountered in Europe and North America are of Type II. Most often the parasite infects warm-blooded animals, including humans, but its definitive host is a felid.

The prevalence of toxoplasmosis varies from one country to another; it is between 60% and 80% in some regions of South America. In Western Europe the prevalence of toxoplasmosis varies from 50 to 70%; it varies from 20 to 50% in Southern Europe and in wet regions in Africa; it is less than 30% in the Scandinavian countries and in the United Kingdom, 25 to 30% in Central European countries and very low in South-East Asia and North America (Pappas et al., 2009).

In France, it is estimated that 40 to 50% of the adult population is infected (source: French National Authority for Health—Haute Autorité de Santé, 2009; Centre *National de Reference de la Toxoplasmose* (CNR)), generally without any apparent symptoms, and that there are between 200 000 and 300 000 new infections each year, including 27 000 cases in pregnant women. Three hundred foetuses suffering from congenital toxoplasmosis (CNR 2011), of whom 30 will develop serious sequelae, are identified every year in France.

In the USA, the prevalence is reported to be 11% in pregnant women born in the USA and 28.1% for those born outside the border limits (Jones et al., 2007). In this country, 1 child out of 10 000 suffers from congenital toxoplasmosis (Brown et al., 2009; Lopez et al., 2000) and ocular toxoplasmosis is the cause of uveitis in 17% of cases and of posterior uveitis in 25% of cases.

While the infection of immunocompetent individuals with Type II strains is generally benign, it can prove to be dramatic in immunodeficient persons or when the immunity system is not yet functional (congenital disorders). In children suffering from congenital toxoplasmosis the disorders are chiefly cerebral and ocular (hydrocephaly, intra-cranial calcifications, convulsions, mental deficiency, chorioretinitis). In addition, the infection of individuals even if they are immunocompetent can be fatal. Finally, temporal cerebral inflammation which occurs during infection with *T. gondii* has recently been positively correlated with a group of neuropsychiatric disorders including schizophrenia (Yolken et al., 2009; Pedersen et al., 2011), bi-polar disorders, neuro-degenerative diseases such as Alzheimer's disease (Kusbeci et al., 2011) and Parkinson's disease (Miman et al., 2010).

It is therefore of importance to be able to make early diagnosis of infection with *T. gondii* so as to set up adequate treatment: combination of pyrimethamine-sulfadiazine and folic acid in patients suffering from congenital toxoplasmosis or in immunodepressed patients, and spiramycin in pregnant women.

The current diagnosis of toxoplasmosis is essentially based on the detection, in the serum of patients, of specific antibodies of G and M isotypes directed against the whole parasite. The level of M immunoglobulins (IgM), in theory the markers of a recent infection, and then of serum G immunoglobulins (IgG) become raised within two weeks following after contamination. While IgMs are the sign of a recent infection (they appear within few days, the peak being reached in 2-3 months after which they decrease), they may persist for several months, even several years and are not therefore reliable indicators of recent seroconversion. In addition, since each patient is different there is no IgG "threshold" level which can be used to distinguish between longstanding infection and recent infection.

The large majority of diagnoses are performed in pregnant women, as part of a multiple diagnosis known as TORCH which targets pathogenic agents able to pass through the placental barrier (T—*Toxoplasma gondii*, O—Other infections (Coxsackievirus, Syphilis, Varicella-Zoster Virus, HIV, Parvovirus B19), R—Rubella, C—Cytomegalovirus, H—Herpes simplex virus). Positive serological tests are supplemented with an IgG avidity test and the search for the presence of the parasite by polymerase chain reaction (PCR) in amniotic fluid in pregnant women or in cerebrospinal fluid in children (only in some countries but not in France) or in immunodepressed individuals suspected of recent infection (Montoya and Remington, 2008).

Most diagnosis kits marketed for toxoplasmosis use parasitic lysates (whole antigens) for the detection of specific antibodies. These kits are sensitive, specific and can be automated but are subject to variations in quality over time and remain costly on account of the preparation mode of the antigens which are subjected to amplification of the parasites in the intra-peritoneal cavity of mice or in cultured human cells. The sensitivity of the assays is also variable.

The use of recombinant proteins as antigens to sensitize supports used for the detection of specific antibodies is therefore undergoing increasing development. Several antigens of *Toxoplasma gondii* have been identified and classified into different families in relation to their cell location:

The antigens of *toxoplasma* dense granules (GRA1, GRA2, GRA3, GRA4, GRA5, GRA6, GRA7, GRA8 . . . )

The surface proteins (SAG1, SAG2, . . . )

The antigens of rhoptria (secretory organelles particular to Apicomplexa) such as ROP1 . . . .

A first type of test, Architect, based on the detection of the major surface protein of the parasite (SAG1) and the dense granule protein GRA8, is marketed by Abbott. Patent application EP 1 082 343 by Abbott describes a diagnostic composition comprising the antigens p29 (GRA7), p30 (SAG1) and p35 (GRA8), or p29 (GRA7), p35 (GRA8) and p66 (ROP1).

The GRA2/p28 antigens (Mercier et al., 1993; FR 2 692 282) and GRA6/p32 (Lecordier et al., 1993; FR 2 702 497) are antigens derived from dense granules, secreted by *T.* gondii and playing an essential role in intracellular parasitism. These are major components of the dense granules (secretory organelles particular to Apicomplexa) and of the vacuole in which the parasite multiples, within the infected cell. These highly immunogenic proteins are good candidates for diagnostic applications.

The recombinant protein GRA2, purified from a bacterial production system, has been tested by ELISA assay, the specificity being 96.4% and sensitivity 95.8% to 100% for acute infections, lower for chronic infections (Golkar et al., 2007). The recombinant protein GRA6 has been tested by ELISA assay and shows much better specificity for sera from patients suffering from acute infection than from those suffering from chronic infection (Golkar et al., 2008).

It has been proposed to associate several recombinant antigens to increase test specificity and sensitivity. In particular, the recombinant protein GRA2 has been associated with the ROP1 (P66) antigen; these two antigens are detected more frequently in sera from patients suffering from acute infection than in sera from patients suffering from chronic infection, thereby allowing a distinction to be made between the two clinical cases (Holec-Gasior et al., 2009). The recombinant protein GRA6 has been associated with GRA1, another antigen of dense granules, in an ELISA assay. This assay, intended to differentiate between patients showing a profile of recent infection and those having a chronic infection, has proved to be insufficiently sensitive for this application (Ferrandiz et al., 2004). The combination of the recombinant antigens GRA2 and GRA6 has been used in a vaccine combination but the antigenic stimulation induced by the combination proved to be disappointing compared with that obtained by injection of the GRA2 protein alone (Golkar et al., 2007).

One of the great challenges in the treatment of toxoplasmosis, in particular in pregnant women, is to initiate treatment as early as possible after the primary infection so as to limit as far as possible the risk of the parasite passing through the placental barrier. This is only possible if diagnosis is made very early. Therefore the development of new assays allowing early diagnosis of the infection will meet a true need of the medical profession. Also, the specificity of known assays must be improved since they still detect too many "false-positives". In particular, for detection in new-borns, it is necessary to distinguish as early as possible between a positive reaction simply due to the presence of maternal antibodies acquired during labour and a true positive reaction related to congenital toxoplasmosis.

SUMMARY

The invention concerns a method for detecting the presence of anti-*Toxoplasma gondii* antibodies in human or animal serum, comprising the contacting of this serum with a composition comprising the recombinant proteins GRA2 and GRA6. More particularly, the invention relates to a direct or indirect ELISA assay (Enzyme-Linked ImmunoSorbent Assay) which allows the early detection in human serum of specific antibodies directed against the antigen combination GRA2 and GRA6. The sensitivity and specificity of this assay allow the envisaged use thereof for confirmation of recent seroconversion in pregnant women and for the diagnosis of congenital toxoplasmosis in new-borns. The first advantage of this assay is its early detection since it allows a very recent infection to be detected in the serum of tested individuals. The second major advantage of this assay is that it allows faster identification of the presence of antibodies in sera from new-borns taken at different times after birth, which has the benefit of excluding or confirming the diagnosis of congenital toxoplasmosis in new-borns.

BRIEF DESCRIPTION OF THE FIGURES

FIGS. 3A-3E: Analysis of eight tests performed on sera from patients with recent seroconversions, in particular 0-1 month and 1-2 month (FIG. 3A); 1-2 month (continued), 2-3 month and 3-4 month (FIG. 3B); 4-5 month, 5-6 month, 6-7 month and 7-8 month (FIG. 3C); 7-8 month (continued), 8-9 month and >9 month (FIG. 3D); and >9 month (continued) (FIG. 3E);

FIGS. 4A-4F: Analysis of women eight tests performed on sera from 32 pregnant women, in particular in patients 1-6 (FIG. 4A); patients 7-12 (FIG. 4B); patients 13-18 (FIG. 4C); patients 19-24 (FIG. 4D); patients 25-31 (FIG. 4E); and patient 32 (FIG. 4F);

FIGS. 5A-5E: Kinetic analysis of eight tests performed on sera from 20 patients with suspected congenital toxoplasmosis, in particular in patients 1-5 (FIG. 5A); patients 5 (continued)-IO (FIG. 54B); patients 10 (continued)-14 (FIG. 5C); patients 15-20 (FIG. 5D); and patient 20 (continued) (FIG. 5E); and FIG. 6: Summary Table of the sensitivity of the ELISA GRA assays.

Figure 1A:
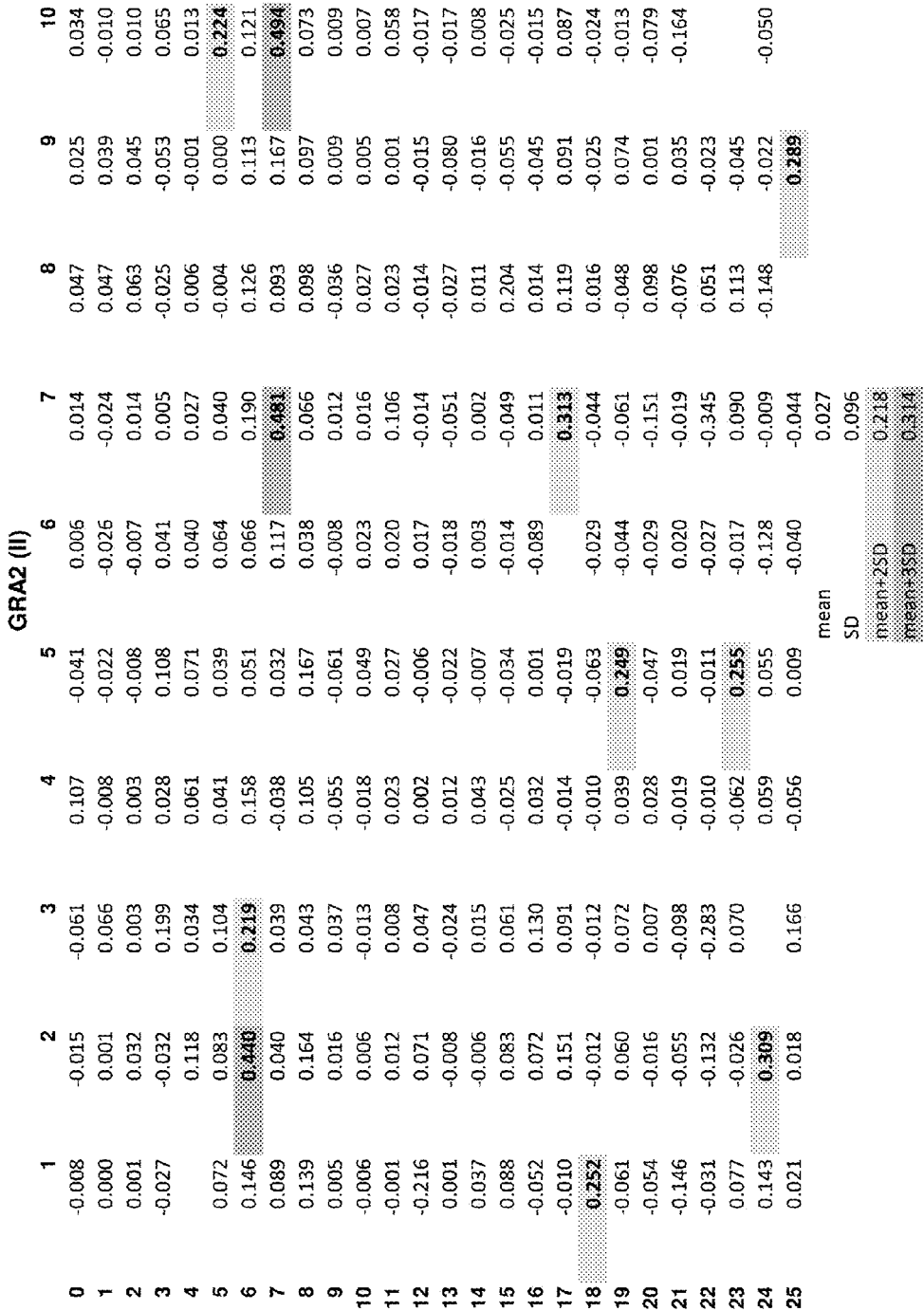
FIG. 1: Summary analysis of 259 negative sera, allowing determination of the positivity threshold (within 2 standard deviations and 3 standard deviations) of each of the 3 ELISA GRA assays and the specificity of each of the 3 assays: (A) GRA (II); (B) GRA6 Nt (II); (C) GRA2+GRA6.

SD: standard deviation; SC: seroconversion, CT: congenital toxoplasmosis Each box gives the number of samples found to be positive with the ELISA GRA assay compared with the number of samples found to be positive with the VIDAS IgG assay (columns "compared with VIDAS IgG") and compared with both IgG assays (columns "compared with (VIDAS+IF) IgG assays").

DETAILED DESCRIPTION

The invention concerns a method for detecting the presence of anti-*Toxoplasma gondii* antibodies in human or animal serum, comprising the contacting of this serum with a composition comprising the recombinant proteins GRA2 and GRA6. The sensitivity and specificity of this method and of the direct or indirect ELISA assay (Enzyme-Linked ImmunoSorbent Assay) which applies this method, allows the use thereof to be envisaged to confirm recent seroconversion in pregnant women, and to diagnose congenital toxoplasmosis in new-borns. The invention concerns a method for identifying the presence or absence of anti-*Toxoplasma gondii* antibodies in human or animal serum, comprising the contacting of the previously sampled serum with antigens capable of binding to the said anti-*Toxoplasma gondii* antibodies, and the determination of the binding or non-binding of antibodies with the said antigens, the method characterized in that the said antigens comprise the combination of two recombinant proteins GRA2 and GRA6.

An antibody is a complex protein produced and used by the immune system specifically to detect and neutralise pathogenic agents. The antibodies are glycoproteins of the immunoglobulin superfamily. They are formed of 4 polypeptide chains: 2 heavy chains and 2 light chains which are linked together by a variable number of disulfide bridges. These chains form a Y-shaped structure. Each light chain is formed of a constant domain and a variable domain; the heavy chains are composed of a variable fragment and of 3 or 4 constant fragments depending on isotype. For a given antibody, the two heavy chains are identical, as is the case for the two light chains. Antibodies have the capability of recognising and binding themselves specifically to an antigen, this specificity being imparted by the presence of the variable domains.

By "anti-*Toxoplasma gondii* antibody", it is meant any antibody capable of bind to an antigen derived from this parasite *Toxoplasma gondii*. This name designates polyclonal and monoclonal antibodies.

By "previously sampled serum" is meant any sample of human or animal blood taken using techniques well known to persons skilled in the art, in particular by means of a syringe, and centrifuged to remove blood cells and coagulation factors. The serum is preferably cold-stored to limit degradation of the proteins. The serum may also be called a "sample" in the present application.

The term "antigen" according to the invention designates any protein derived from *Toxoplasma gondii* or any recombinant protein synthesised from DNA of *Toxoplasma gondii*, and able to induce an immune response in an infected individual. An antigen generally has several different epitopes which form as many binding sites to the antibodies.

The term "binding of antibodies with the said antigens" designates the interaction between an antigen and an antibody specific to this antigen, and more specifically the immune complex resulting from the combination of an immunogenic epitope of the antigen with an antibody specifically directed against this epitope.

The two proteins GRA2 and GRA6 refer to proteins with strong antigenic properties of *Toxoplasma gondii*, such as described in the foregoing.

The term "recombinant proteins" designates proteins produced in genetically modified cells, in particular via insertion of an expression vector carrying a gene of interest. This gene encoding a protein of interest is expressed by the producing species (bacteria, cultured mammalian cells, etc.). Preferably, the recombinant proteins are produced in a bacterial system and in particular in *Escherichia coli*. After purification, they are used to "capture" the antibodies potentially present in a human or animal serum.

The antigens present in the method of the invention comprise at least the recombinant proteins GRA2 and GRA6, but they may also comprise other recombinant proteins such as GRA1, GRA3, GRA4, GRA5, GRA7, GRA8, etc. According to one preferred aspect of the invention, the method is characterized in that the antigens are only formed of the combination of the two recombinant proteins GRA2 and GRA6.

The GRA2 and GRA6 proteins may be present in any proportion and in particular the GRA2/GRA6 molar ratio may be 10:90, 20:80, 30:70, 40:60, 50:50, 60:40, 70:30, 80:20, or 90:10. According to one preferred aspect of the invention, the GRA2/GRA6 molar ratio is comprised between 40:60 and 60:40. According to one preferred aspect of the invention, the GRA2/GRA6 molar ratio is 50:50.

The above-described method can be implemented using any type of immunological assay known to the person skilled in the art, such as radio-immunological assays which use radioactive compounds associated with antigens, or immuno-enzymatic assays which use enzymes coupled with antigens. The method to detect the presence or absence of anti-*Toxoplasma gondii* antibodies in a serum, also called antibody assay method, can be implemented in a solution or on a solid support. The invention relates in particular to a method characterized in that the antigens are attached onto a support. This support is preferably an ELISA assay plate.

The ELISA immuno-enzymatic assay ("Enzyme-linked immunosorbent assay") is conventionally used in immunology to detect and assay an antibody or antigen in a sample. This test is characterized by the fact that the assay is coupled with a reaction catalysed by an enzyme which releases a stained component, followed by spectroscopy. The ELISA is generally based on the use of two antibodies: one thereof is specific to the antigen, whilst the other reacts with the immune complexes (antigen-antibody) and is coupled to an enzyme. This secondary antibody, responsible for the name of the technique, can also cause the emitting of a signal by a chromogenic or fluorogenic support.

Several ELISA techniques are known to those skilled in the art, such as direct ELISA, indirect ELISA, sandwich ELISA or competitive ELISA. The steps of indirect ELISA, the most frequently used technique to determine the antibody concentration of serum, are:

1. applying a known antigen onto a surface, most often the well of a micro-titration plate. The antigen is attached to the surface so that it is immobile;
2. saturating sites not occupied by the antigen with a non-specific protein, generally bovine serum albumin;
3. covering the wells with serum samples to be tested, the antibody concentration of which, by definition, is unknown;
4. rinsing the plate, so as to remove non-bound antibodies. After rinsing, solely the antigen-antibody complexes remain attached to the surface of the well;
5. adding secondary antibodies to the wells which will bind to the primary antibody (in this case, it is an anti-immunoglobulin antibody). These secondary antibodies are coupled with the support-modifying enzyme allowing the monitoring of the progress of the reaction;
6. second rinsing of the plate, so as to remove non-bound antibodies;
7. applying a support which, if converted by the enzyme, emits a chromogenic or fluorescent signal;
8. quantifying the result by spectrophotometer or any other optical apparatus. The enzyme acts as amplifier: even if few antibodies conjugated with the enzyme were attached, the enzyme would catalyse the formation of numerous signals, which makes this assay very sensitive but also increases the number of false-positives. "Control" wells must therefore be provided.

In the method of the invention, preferably the determination of the presence or absence of antibody binding to said antigens comprises the application of reagents allowing the detection of those antibodies attached to the recombinant proteins. In particular, these reagents allow determination of the quantity of antibodies present in the serum. According to one preferred aspect of the invention, the serum is from a pregnant woman. According to another preferred aspect of the invention, the serum is from a new-born.

In particular, the method of the invention can advantageously be used for the early diagnosis of congenital toxoplasmosis. The term "early" indicates that the diagnosis can be made very early during the first months after birth. The method of the invention can also be characterized in that it is performed in addition to another test to diagnose toxoplasmosis. Indeed, this assay is preferably a "second intention" assay having a very good sensitivity with regard to recently infected sera. This diagnosis assay will preferably be proposed in particular situations in which a recent seroconversion is suspected, as an additional test to routine diagnosis tests.

The present invention also relates to a kit intended to identify the presence or absence of anti-*Toxoplasma gondii* antibodies in a human or animal serum, comprising:

A support (ELISA plate) on which the recombinant proteins GRA2 and GRA6 are attached;

Reagents allowing the detection of antibodies which bind to the recombinant proteins.

Preferably, the recombinant proteins GRA2 and GRA6 will have a molar ratio comprised between 40:60 and 60:40 in this kit.

ELISA Protocol

ELISA Protocol

The solid support is coated overnight at 4° C. with a solution comprising:
  100 µL of GRA2 (21-185) (II) denoted GRA2 (II), or of
  protein GRA6 (41-152) (II) denoted GRA6 Nt (II), or of
  a 50:50 mixture of GRA2 (II) and GRA6 Nt (II) denoted GRA2+GRA6 Nt (II),
i.e. 1.5 µg of proteins dialysed in PBS then diluted in carbonate buffer pH 9.6, or an equivalent number of moles of peptide pUET (=0.5 µg) dialysed in PBS.

The recombinant proteins GRA2 and GRA6 are indeed fused to the pUET peptide and thus purified after synthesis: for better assay accuracy, the absorbance value of the pUET peptide is inferred from absorbency values obtained with GRA2 (II), GRA6 (II) or the mixture.

The solid support is washed three times with conventional PBS+0.05%

Tween 20 buffer (PBS-T) by a washer.

The blocking of non-specific sites is obtained with bovine serum albumin (BSA) at a concentration of 1%, for one hour at 37° C.

The support is washed three times in PBS-T buffer.

Incubation of human serum: at 37° C., for 1 h: 100 µL 1:50 human serum in PBS-T, 0.5% BSA, 5% (v/v) bacterial lysate 4 µg/ml.

The support is washed three times in PBS-T buffer.

Incubation of the conjugated antibody. At 37° C., for 1 h. 100 µL rabbit anti-human IgG serum (H+L)—peroxidase (Jackson) 1:30,000.

The support is washed three times in PBS-T buffer.

Detection. 10 min, Ambient temperature, in the dark: 100 µL 1-Step Ultra TMB, with halting of reaction by adding 50 µL of 3 M HCl.

Result reading at Optical Density of 450 nm, ref 630 nm.

EXAMPLES

Several assays were conducted on a total of 860 human sera collected at the Parasitology and Mycology Department of Hospital Michallon, during routine analyses (sera of pregnant women, of children suspected of having congenital toxoplasmosis, HIV-positive patients, patients awaiting grafts, etc.). These sera included:

259 sera tested negative after routine analysis i.e. the detection threshold of the tests used did not allow the evidencing of the presence of anti-toxoplasmosis antibodies;

253 sera diagnosed as positive for longstanding toxoplasmosis i.e. dating from more than twelve months (i.e. sera for which positive IgG levels had been detected but without IgM.);

122 sera for which the seroconversion date could be estimated as recent i.e. less than 1 year (distribution in one-month intervals); among these 122 sera, 120 were IgG positive under routine testing (ELFA VIDAS and/or IFI);

120 sera originating from 32 patients monitored sequentially over several sampling times, to detect seroconversion during pregnancy; among these 120 sera, 79 were IgG positive under routine testing (ELFA VIDAS and/or IFI);

106 samples taken from 20 new-borns suspected of congenital toxoplasmosis (finally 10 confirmed cases of congenital toxoplasmosis and 10 negative cases). Amongst these 106 sera, 90 were IgG positive under routine testing (ELFA VIDAS and/or IFI).

The method of the invention is an assay for which the sensitivity for recently infected sera and specificity are particularly good. The sensitivity of an assay is its ability to give a positive result when the disease (here infection with *Toxoplasma gondii*) is present. The specificity of an assay is the ability of the assay to give a negative result when the disease is not present.

The examples given below illustrate the good performance of the method of the invention.

Example 1

Summary Analysis of 259 Negative Results, Allowing Determination of the Positivity Threshold for Each of the 3 ELISA GRA Assays (to within 2 Standard Deviations and 3 Standard Deviations) and the Specificity of Each of the 3 Assays Thresholds of Commercial Assays Used:
Threshold of ELFA Vidas IgG assay (bioMérieux):
  OD<4 UI/ml negative;
  OD>7 UI/ml positive,
  OD=4-7 UI/ml equivocal
Threshold of IFI IgG assay (Indirect immunofluorescence): 8 UI/ml
Threshold of ELISA Vidas IgM assay (bioMérieux):
  OD<0.55 negative;
  OD>0.65 positive;
  OD=0.55-0.65 equivocal
Threshold of IFI IgM assay: 1/40
Threshold of ISAGA IgM assay (bioMérieux): 9

The values given in the Tables can be analysed taking into account the positivity thresholds listed above. These values define the detected quantity of antibody which is sufficiently significant to indicate infection with *Toxoplasma gondii*. By comparison, the results given in FIG. 1 allow the determination of the positivity thresholds and of the specificity of the assays of the present invention.

Positivity Threshold and Specificity of ELISA GRA Assays Developed by the Inventors:

The specificity of the ELISA GRA assay is calculated by dividing the number of sera found to be negative with the ELISA GRA assay by the number of negative sera with the ELISA assay, multiplied by 100.

Positivity threshold of ELISA GRA2 (II)—results in FIG. 1A:

$A_{450}$=0.218 (2 standard deviations, figures in bold in the Table); and $A_{450}=0.314$ (3 standard deviations, figures in bold and darker cell background).

Out of the 253 sera which tested negative with routine testing, 3 are above the positivity threshold of the ELISA GRA2 (II) assay (3 SD). Therefore the specificity is: 250/253×100=98.81%

Positivity threshold of ELISA GRA6 Nt (II)—results in FIG. 1B:

$A_{450}=0.422$ (2 standard deviations, figures in bold in the Table); and $A_{450}=0.604$ (3 standard deviations, figures in bold and darker cell background).

Out of the 253 sera which tested negative under routine testing, 6 are above the positivity threshold of the ELISA GRA6 Nt (II) assay (3 SD); the specificity of the assay if therefore: 247/253×100=97.62%

Figure 1C:
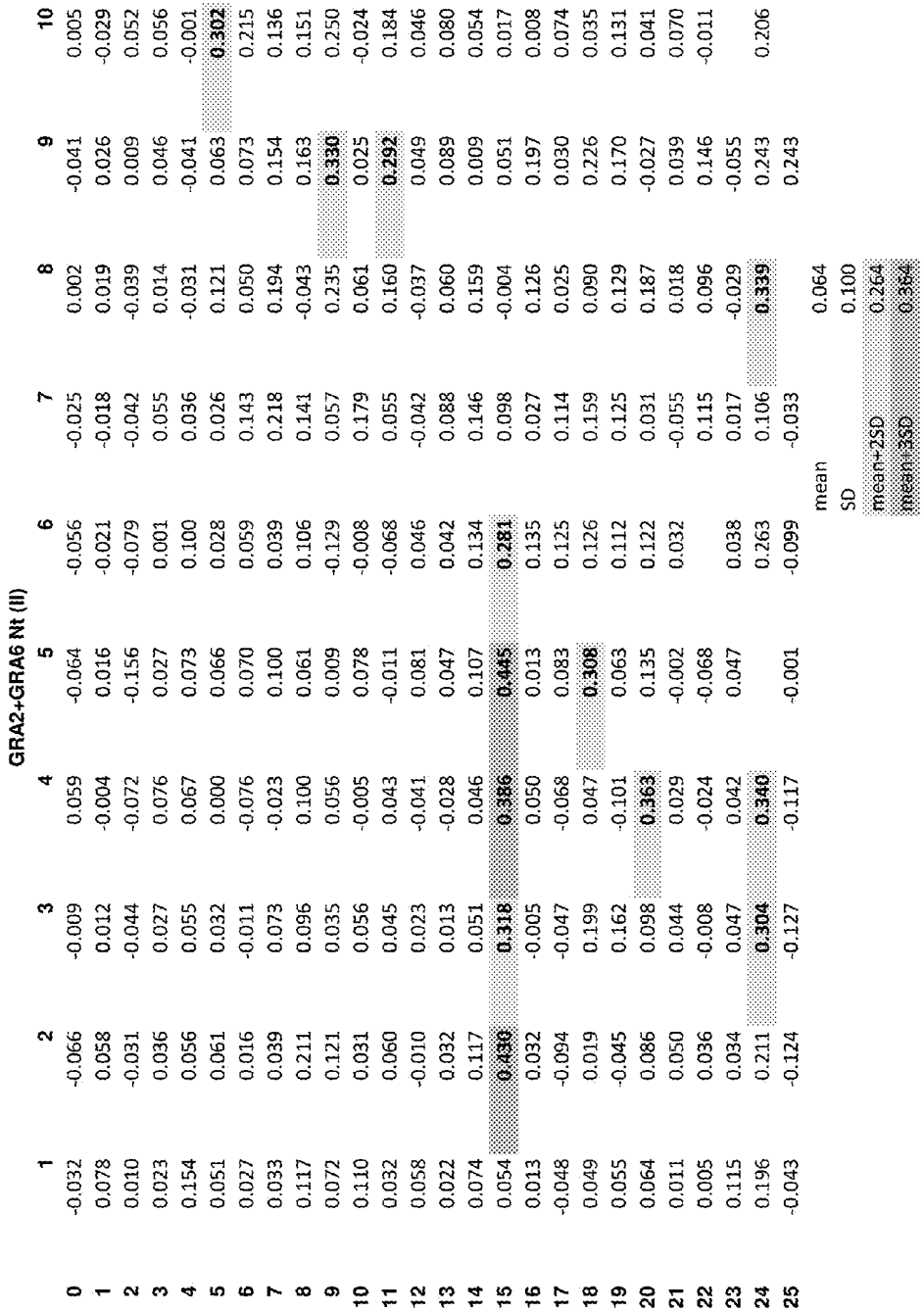

Positivity threshold of ELISA GRA2+GRA6 Nt (II)—results in FIG. 1C:

$A_{450}=0.264$ (2 standard deviations, figures in bold in the Table); and $A_{450}=0.364$ (3 standard deviations, figures in bold and darker cell background).

Out of 255 sera found negative with routine testing, 3 are above the positivity threshold of the ELISA GRA6 Nt (II) assay (3 SD); hence assay specificity of: 252/255×100=98.82%

The sensitivity of an assay is calculated by dividing the number of samples found positive with the assay (ELISA GRA) by the number of samples found positive in control diagnosis assays, multiplied by 100. The difficulty with the diagnosis of toxoplasmosis is that there is no control assay. It is the accumulation of the results of 5 different assays seeking to identify both IgMs and IgGs with patient follow-up over time, which allows the determination of whether or not the patient is infected and if so since when. However the sensitivity of our ELISA GRA assays will nevertheless be defined:

in relation to the VIDAS IgG assay, even if this assay is known to have late IgG detection (whereas the IF IgG assay, which detects IgGs directed against the surface proteins of the parasite shows earlier positivity):

in relation to both IgG assays routinely performed in the laboratory (VIDAS IgG and IF IgG) (see FIG. 6).

The results given below tend to prove that:

The sensitivity of the 3 ELISA GRA assays over all the tested sera is most variable depending on whether sera are considered of longstanding infection (low sensitivity, 86.56% for the GRA2+GRA6 Nt (II) assay (cf. FIG. 6), of recent seroconversion or sera from new-borns suspected of having congenital toxoplasmosis (sensitivity higher than 100% for the GRA2+GRA6 Nt (II) assay since it detects more sera than routine assays (cf. FIG. 6).

on the other hand, the ELISA GRA2+GRA6 Nt (II) assay exhibits very good sensitivity for very recently infected sera, which supports the proposing of this diagnosis assay in particular situations in which recent seroconversion is suspected, as an additional assay to routine diagnosis testing (see FIG. 6).

Example 2

Analysis of 253 Chronic Sera (Taken from Persons Infected for More than 12 Months)

Figure 2A:
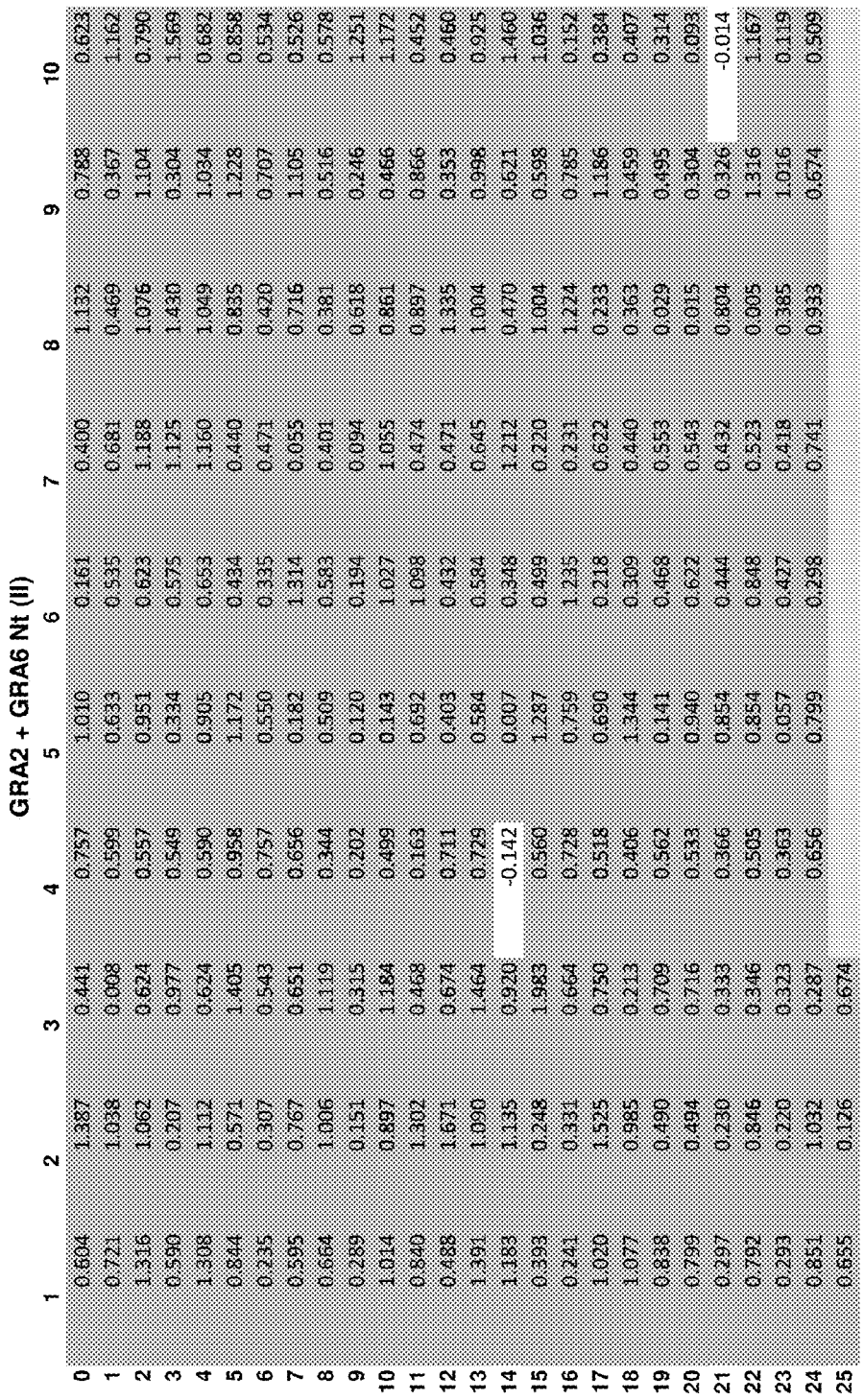
FIG. 2: Summary analysis of 253 chronic infection sera (infections dating back to more than 12 months: sera positive for IgG with routine tests but negative for IgM) allowing demonstration that the ELISA GRA assays are not adapted for first intention diagnosis; (A) ELISA GRA2+GRA6; (B) IgG Vidas.
Figure 2B:
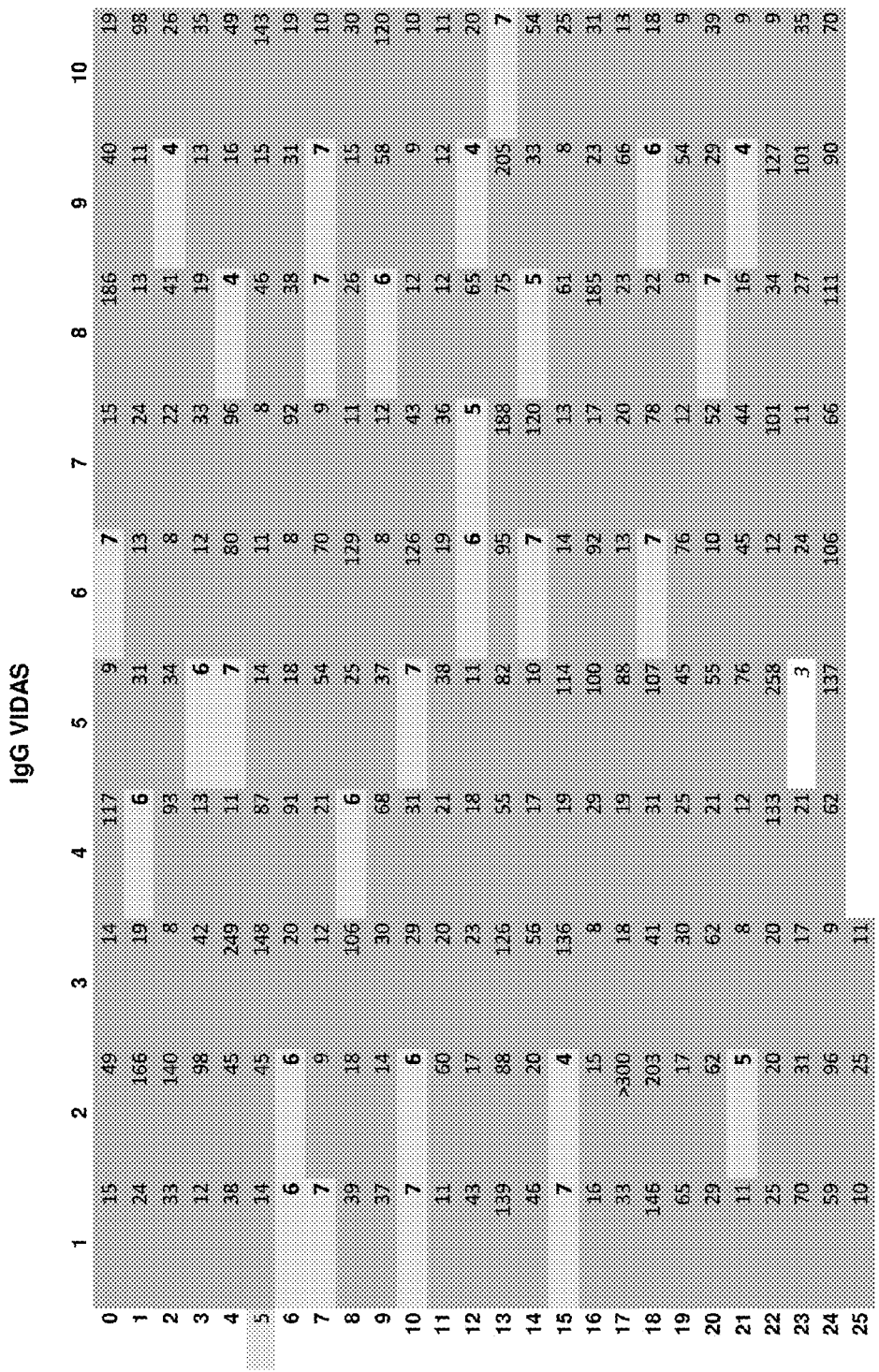

FIGS. 2A and 2B give the analysis of 253 sera with longstanding infection, using two different assays:

ELISA IgG GRA2+GRA6 Nt (II)—see FIG. 2A

The kit marketed by Biomérieux, "ELFA IgG VIDAS®", called "Biomérieux kit" in the remainder hereof.—see results in FIG. 2B.

This kit uses the "ELFA" assay principle associating the ELISA method with final reading under blue fluorescence. The positivity threshold of the kit is 4-8 UI/mL It allowed the detection of:

1 negative serum (figure in italics, white cell background);

29 sera having a content of between 4 and 8 UI/mL, hence "equivocal" (figures in bold, light grey cell background);

223 sera with a content higher than 8 UI/mL i.e. positive (dark grey cell background).

The ELISA GRA2+GRA6 Nt (II) assay (FIG. 2A) has a positivity threshold of 0.364 (3 SD) and 0.264 (2 SD). It detected 77.07% of longstanding infections whereas the Biomérieux kit detected 88.14%, in the "Pos. 3 SD" category, i.e. with a positivity threshold of the assay at the mean absorbance value of 255 negative sera+3 standard deviations as presented in the foregoing (0.264 for 2 SD, 0.364 for 3 SD).

Figure 4A:
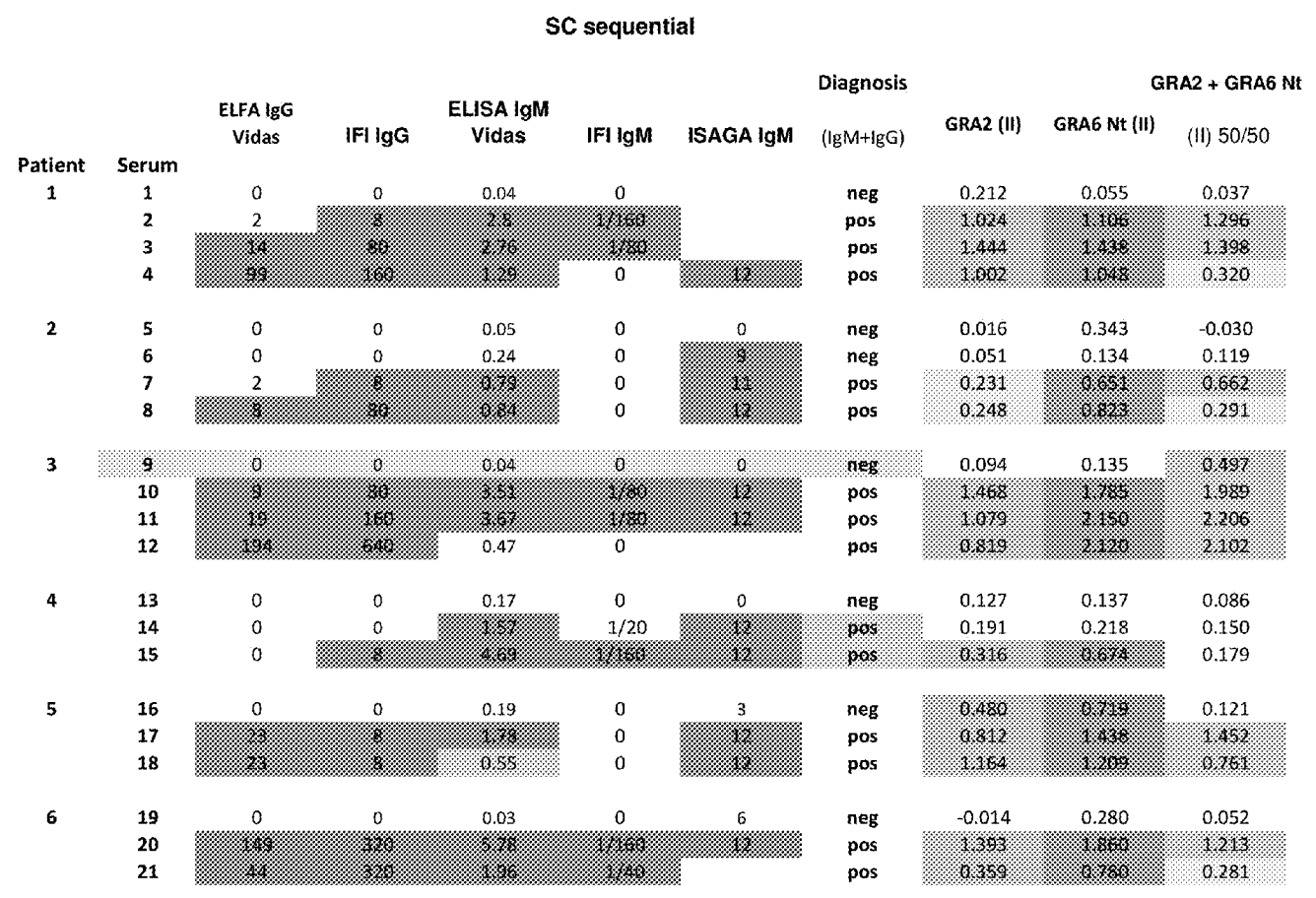

If the threshold is lowered to only 2 standard deviations, the ELISA GRA2+GRA6 Nt (II) detected 86.56% of longstanding infections whereas the Biomérieux kit detected 99.6%. It therefore appears that the ELISA GRA2+GRA6 Nt (II) assay is not suitable for detecting longstanding infections. The Tables given in FIGS. 3, 4 and 5 detail the data derived from the analysis of the different sera having recent infection.

Example 3

Analysis of 122 Dated Seroconversions (Including 120 Samples Testing Positive for IgG The results are given in FIGS. 3A-3E. Eight assays, the thresholds of which are recalled between brackets, were performed in parallel on each serum:

ELISA IgG Vidas (4-8 UI/ml equivocal)

IFI IgG (8 UI/ml)

ELISA IgM Vidas (0.55-0.65 OD equivocal)

IFI IgM (DiI 1/40)

ISAGA IgM (9)

GRA2 (II) (0.218-0.314)

GRA6 Nt (II) (0.422-0.604)

GRA2+GRA6 Nt (II) 50/50 (0.264-0.364)

For the ELISA GRA assays:

the dark cell backgrounds represent the absorbance values above the positivity threshold (3 SD).

the light colours represent the absorbance values between the positivity threshold (2 SD) and the positivity threshold (3 SD).

For routine testing:

the dark cell background colours represent positive values;

the light colours represent values lying in the equivocal region if such exists.

The cells with white background represent the results obtained below the threshold of each assay. The darker background lines are those for which sera are missing.

ELISA GRA2 (II)

90 positive sera (3 SD) out of 120 positive for IgG under routine testing 90+11=101 positive sera (2 SD) out of 120 sera positive for IgG under routine testing ELISA GRA6 Nt (II)

105 positive sera (3 SD) out of 120 positive for IgG under routine testing 105+0=105 positive sera (2 SD) out of 120 positive for IgG under routine testing ELISA GRA2+GRA6 Nt (II)

121 positive sera (3 SD) out of 120 positive for IgG under routine testing 121+0=121 positive era (2 SD) out of 120 positive for IgG under routine testing VIDAS IgG 102 positive sera (3 SD) out of 120 positive for IgG under routine testing 102+8=110 positive sera (2 SD) out of 120 positive for IgG under routine testing Results Obtained with the ELISA IgG GRA2 (II)+GRA6 Nt (II) Assay Positivity higher than 2 standard deviations: 121/120=100.83%

Positivity higher than 3 standard deviations: 121/120=100.83%

Equivocal: 0/120=0%

Negative: 1/120=0.83%

Results Obtained with the BioméRieux Assay (ELFA Vidas IgG)

Positivity higher than 2 standard deviations: 110/120=90.66%

Positivity higher than 3 standard deviations: 102/120=85%

Equivocal: 8/120=6.66%

Negative: 12/120=10%

If consideration is given to the pos.>3SD, the GRA2+GRA6 Nt (II) assay is therefore more sensitive and allows earlier detection of the infection than ELFA IgG VIDAS. If the results are examined in more detail, by comparison with the ELFA IgG Vidas assay, the GRA2+GRA6 NT (II) assay allows the "recovery" of:

8 sera between 0 and 1 month, including 2 still negative with IFI IgG (all positive for IgM)

3 sera between 1 and 2 months (positive for IgM), 1 serum between 6 and 7 months (positive for IgM and with IF IgG)

The GRA2+GRA6 assay therefore allows the identification of sera considered to be "negative" for IgG with another assay, but which were in fact "positive" for infection with *Toxoplasma gondii* and for which diagnosis was solely based on IgM detection. This is due to the fact that the assay developed by the inventors has better sensitivity for recently infected sera (higher than 100% since it allows the detection of more samples than routine testing) than the assays currently marketed (between 85 and 91.66%, depending on the standard deviations taken into consideration).

Example 4

Analysis of 120 Sera of Sequential Seroconversions Taken from 32 Patients (79 Sera Positive for IgG Under Routine Testing)

The results are given in FIGS. 4A-4F. The assays were performed on sera from 32 pregnant women. For each one 3 to 5 serum samples were tested. For 11 patients the ELISA GRA2+GRA6 Nt (II) assay allowed earlier detection of the infection than routine testing.

Eight assays, for which the thresholds are recalled in brackets, were performed in parallel on each serum:

ELISA IgG Vidas (4-8 UI/ml equivocal)

IFI IgG (8 UI/ml)

ELISA IgM Vidas (0.55-0.65 OD equivocal)

IFI IgM (DiI 1/40)

ISAGA IgM (9)

GRA2 (II) (0.218-0.314)

GRA6 Nt (II) (0.422-0.604)

GRA2+GRA6 Nt (II) 50/50 (0.264-0.364)

A ninth column indicates the diagnosis made by practitioners without taking into account the results obtained afterwards with the ELISA GRA2 (II), GRA6 Nt (II) and GRA2+GRA6 Nt (II) assays. The same colour codes as in FIG. 3 are used. Results for 120 sera of which 79 were positive for IgG under routine testing:

ELISA GRA2 (II)

75 positive sera (3 SD) out of 79 positive for IgG under routine testing 75+12=87 positive sera (2 SD) out of 79 sera positive for IgG under routine testing ELISA GRA6 Nt (II)

78 positive sera (3 SD) out of 79 positive for IgG under routine testing 78+8=86 positive sera (2 SD) out of 79 positive for IgG under routine testing ELISA GRA2+GRA6 Nt (II)

85 positive sera (3 SD) out of 79 positive for IgG under routine testing 85+9=94 positive sera (2 SD) out of 79 positive for IgG under routine testing VIDAS IgG 56 positive sera (3 SD) out of 79 positive for IgG under routine testing 56+6=62 positive sera (2 SD) out of 79 positive for IgG under routine testing For patient Nos 3, 14, 16, 20, 21, 22, 27, 28, 30, 31 (10 patients/32 of which 3 patients with 2 SD): the ELISA IgG GRA2+GRA6 Nt (II) assay proved positive even before IgM detection. In particular, four samples were taken from patient No 3 at one-month intervals. When testing the $1^{st}$ serum using the Biomérieux kit, the serum was considered to be negative for the presence of anti-*Toxoplasma gondii* IgG. Yet, as early as this first sampling the GRA2+GRA6 Nt (II) assay indicated the presence of anti-GRA IgG antibodies. For patient No 23 (only positive with highly sensitive ISAGA IgM), the GRA2+GRA6 Nt (II) assay indicated the presence of anti-GRA IgG antibodies. For patient Nos 1, 7, 9, 15, 17, 18, 19, 24, 29, 32 (10 patients/32): positive diagnosis was only found for IgMs, or for IgMs and a IgG threshold value with IFI. The ELISA IgG GRA2+GRA6 Nt (II) assay would have allowed diagnosis by evidencing early anti-Gra IgGs.

In particular, four samples were taken from patient No 1 at 1 month-intervals. When testing the $1^{st}$ serum using the Biomérieux kit and the GRA2+GRA6 Nt (II) kit, the serum was considered negative for anti-*Toxoplasma gondii* IgGs. At the testing of the second serum, on the contrary, the values were still below the detection threshold of the Biomérieux kit but they indicated the presence of anti-Gra IgG antibodies when using the GRA2+GRA6 Nt (II) kit. For patient Nos 1 and 8: the ELISA IgG GRA2+GRA6 Nt (II) assay was negative at the same time as the IFI IgM if the positivity threshold is considered to be 3 SD, but it remained positive at 2 SD. There is therefore a substantial decrease in the amount of IgGs directed against GRA2 (II) and GRA6 Nt (II).

Example 5

Kinetic Analysis of 106 Samples of Congenital Toxoplasmosis (10 Cases+, 10 Cases −) Including 90 Samples Positive for IgG Under Routine Testing The results obtained are given in FIGS. 5A-5E. The same colour codes are used as in FIGS. 3A-3E.

ELISA GRA2 (II)

60 positive sera (3 SD) out of 90 positive for IgG under routine testing 60+7=67 positive sera (2 SD) out of 90 sera positive for IgG under routine testing ELISA GRA6 Nt (II)

63 positive sera (3 SD) out of 90 positive for IgG under routine testing 63+7=70 positive sera (2 SD) out of 90 positive for IgG under routine testing ELISA GRA2+GRA6 Nt (II)

77 positive sera (3 SD) out of 90 positive for IgG under routine testing 77+4=81 positive sera (2 SD) out of 90 positive for IgG under routine testing VIDAS IgG 76 positive sera (3 SD) out of 90 positive for IgG under routine testing 76+10=86 positive sera (2 SD) out of 90 positive for IgG under routine testing The ELISA IgG GRA2+GRA6 NT (II) assay becomes negative quicker than the ELFA IgG Vidas assay: the case for patients 4, 5, 8, 12, 13, 16, 20 (7/10 CT—with 3 SD and 9/10 with 2 SD)). For example, patient No 8 was diagnosed positive for IgG at birth (sample No 37) and was therefore given follow-up although this patient was already negative with the ELISA GRA2+GRA6 Nt (II) assay. The IgGs detected under routine testing (VIDAS IgG and IF IgG) were therefore residual IgGs of the mother which passed into the bloodstream of the child during labour. These IgGs are naturally eliminated after a few weeks.

Similarly, patient No 12 was diagnosed positive for anti-*Toxoplasma gondii* IgG under routine testing up until sample No 64, whereas this patient would have been diagnosed negative as early as sample No 63 with the ELISA GRA2+GRA6 Nt (II) assay. To be noted is the case of patient No 20: re-onset of IgGs after they became negative.

PATENT REFERENCES

FR 2 692 282
FR 2 702 497

BIBLIOGRAPHICAL REFERENCES

Pappas G. Roussos N, Falagas M E "*Toxoplasmosis snapshots: global status of Toxoplasma gondii seroprevalence and implications for pregnancy and congenital toxoplasmosis.*" International Journal for Parasitology [2009, 39(12):1385-1394].

Jeffrey L. Jones, Deanna Kruszon-Moran, Kolby Sanders-Lewis and Marianna Wilson. "*Toxoplasma gondii Infection in the United States, 1999-2004, Decline from the Prior Decade*"; Am J Trop Med Hyg September 2007 vol. 77 no. 3 405-410.

Brown E D, Chau J K, Atashband S, Westerberg B D, Kozak F K "*A systematic review of neonatal toxoplasmosis exposure and sensorineural hearing loss.*" International Journal of Pediatric Otorhinolaryngology [2009, 73(5): 707-711].

Lopez A, Dietz V J, Wilson M, Navin T R, Jones J L. "*Preventing congenital toxoplasmosis.*" MMWR Recomm Rep. 2000 Mar. 31; 49(RR-2):59-68.

R. H. Yolken, F. B dickerson, E. Fuller Torrey "*Toxoplasma and schizophrenia*" Parasite Immunology Volume 31, Issue 11, pages 706-715, November 2009.

Marianne Giørtz Pedersen, M. Sc.; Hanne Stevens, M. Sc.; Carsten Bøcker Pedersen, Dr. Med. Sc.; Bent Nørgaard-Pedersen, Dr. Med. Sc.; Preben Bo Mortensen, Dr. Med. Sc. "*Toxoplasma* Infection and Later Development of Schizophrenia in Mothers" Am J Psychiatry 2011; 168: 814-821.

Kusbeci, Ozge Yilmaz MD; Miman, Ozlem MD, PhD; Yaman, Mehmet MD; Aktepe, Orhan Cem MD; Yazar, Suleyman MD, PhD "Could *Toxoplasma gondii* Have any Role in Alzheimer Disease?" Alzheimer Disease & Associated Disorders: January-March 2011—Volume 25—Issue 1—p 1-3.

O Miman, O Y Kusbeci, O C Aktepe, Z Cetinkaya—"*The probable relation between Toxoplasma gondii and Parkinson's disease*" Neuroscience letters, 2010 Elsevier.

Jose G. Montoya and Jack S. Remington—"*Management of Toxoplasma gondii Infection during Pregnancy*" Clin Infect Dis. (2008) 47 (4): 554-566.

Corinne Mercier, Laurence Lecordiera, Françoise Darcya, Didier Desleea, Avril Murraya, Béatrice Tourvieillea, Pierrette Maesb, André Caprona, Marie-France Cesbron-Delauw "*Molecular characterization of a dense granule antigen (Gra 2) associated with the network of the parasitophorous vacuole in Toxoplasma gondii*" Molecular and Biochemical Parasitology, Volume 58, Issue 1, March 1993, Pages 71-82.

Laurence Lecordier; Corinne Merciera, Gérard Torpiera, Béatrice Tourvieillea, Francoise Darcya, Liu Jin Lia, Pierette Maesb, André Tartarb, André Caprona, Marie-France Cesbron-Delauw "*Molecular structure of a Toxoplasma gondii dense granule antigen (GRA 5) associated with the parasitophorous vacuole membrane*" Molecular and Biochemical Parasitology Volume 59, Issue 1, May 1993, Pages 143-153.

Golkar M, Rafati S, Abdel-Latif M S, Brenier-Pinchart M P, Fricker-Hidalgo H, Sima B K, Babaie J, Pelloux H, Cesbron-Delauw M F, Mercier C. "*The dense granule protein GRA2, a new marker for the serodiagnosis of acute Toxoplasma infection: comparison of sera collected in both France and Iran from pregnant women.*" Diagn Microbiol Infect Dis. 2007 August; 58(4):419-26.

Golkar M, Azadmanesh K, Khalili G, Khoshkholgh-Sima B, Babaie J, Mercier C, Brenier-Pinchart M P, Fricker-Hidalgo H, Pelloux H, Cesbron-Delauw M F. "*Serodiagnosis of recently acquired Toxoplasma gondii infection in pregnant women using enzyme-linked immunosorbent assays with a recombinant dense granule GRA6 protein.*" Diagn Microbiol Infect Dis. 2008 May; 61(1):31-9.

Holec-Gasior L, Kur J, Hiszczyńska-Sawicka E. "*GRA2 and ROP1 recombinant antigens as potential markers for detection of Toxoplasma gondii-specific immunoglobulin G in humans with acute toxoplasmosis.*" Clin Vaccine Immunol. 2009 April; 16(4):510-4.

Ferrandiz J, Mercier C, Wallon M, Picot S, Cesbron-Delauw M F, Peyron F. "*Limited value of assays using detection of immunoglobulin G antibodies to the two recombinant dense granule antigens, GRA1 and GRA6 Nt of Toxoplasma gondii, for distinguishing between acute and chronic infections in pregnant women.*" Clin Diagn Lab Immunol. 2004 November; 11(6):1016-21.

Golkar M, Shokrgozar M A, Rafati S, Musset K, Assmar M, Sadaie R, Cesbron-Delauw M F, Mercier C. "*Evaluation of protective effect of recombinant dense granule antigens GRA2 and GRA6 formulated in monophosphoryl lipid A (MPL) adjuvant against Toxoplasma chronic infection in mice.*" Vaccine. 2007 May 22; 25(21):4301-11.

The invention claimed is:

1. A method for identifying the presence or absence of anti-*Toxoplasma gondii* antibodies in human or animal serum, the method comprising: obtaining a serum sample from a patient, contacting the serum sample with a composition comprising antigens capable of binding to said anti-*Toxoplasma gondii* antibodies and determining antibody binding or non-binding to said antigens, wherein said antigens comprise a combination of two recombinant proteins GRA2 and GRA6.

2. The method according to claim 1, wherein said antigens consist of a combination of the two recombinant proteins GRA2 and GRA6.

3. The method according to claim 1, wherein the GRA2/GRA6 molar ratio is between 40:60 and 60:40.

4. The method according to claim 3, wherein said GRA2/GRA6 molar ratio is 50:50.

5. The method according to claim 1, further comprising attaching said antigens to a support.

6. The method according to claim 1, wherein said determining of said binding or non-binding of said antibodies to said antigens comprises applying detection reagents to the serum and antigens, wherein the detection reagents cause a signal to be emitted when anti-*Toxoplasma gondii* antibodies are bound to the antigens.

7. The method according to claim 1, wherein the patient is a pregnant woman.

8. The method according to claim 1, wherein the patient is a new-born.

9. The method according to claim 1, further comprising implementing said method in addition to another diagnostic test for toxoplasmosis.

10. A kit for identifying the presence or absence of anti-*Toxoplasma gondii* antibodies in a human or animal serum, comprising:
- a support on which recombinant proteins GRA2 and GRA6 are attached; and
- detection reagents that cause a signal to be emitted when anti-*Toxoplasma gondii* antibodies are bound to the recombinant proteins GRA2 and GRA6.

\* \* \* \* \*